United States Patent
Delwart et al.

(10) Patent No.: US 8,614,090 B2
(45) Date of Patent: Dec. 24, 2013

(54) ASTROVIRUS SPECIES

(75) Inventors: Eric Delwart, San Francisco, CA (US);
Amit Kapoor, New York, NY (US); Li Linlin, San Francisco, CA (US)

(73) Assignee: Blood Systems, Inc., Scottsdale, AZ (US)

( * ) Notice: Subject to any disclaimer, the term of this patent is extended or adjusted under 35 U.S.C. 154(b) by 410 days.

(21) Appl. No.: 12/859,068

(22) Filed: Aug. 18, 2010

(65) Prior Publication Data

US 2011/0045018 A1     Feb. 24, 2011

Related U.S. Application Data

(60) Provisional application No. 61/235,126, filed on Aug. 19, 2009.

(51) Int. Cl.
| *C07H 21/04* | (2006.01) |
|---|---|
| *A61K 39/12* | (2006.01) |
| *C12Q 1/68* | (2006.01) |
| *C12Q 1/70* | (2006.01) |
| *C12N 7/00* | (2006.01) |
| *C12N 5/00* | (2006.01) |
| *C12N 15/00* | (2006.01) |

(52) U.S. Cl.
USPC ............ 435/320.1; 435/5; 435/6.1; 435/6.11; 435/6.12; 435/6.13; 435/235.1; 435/325; 536/23.72; 536/24.3; 536/24.32; 536/24.33

(58) Field of Classification Search
None
See application file for complete search history.

(56) References Cited

U.S. PATENT DOCUMENTS

| 5,625,049 | A | 4/1997 | Monroe et al. |
|---|---|---|---|
| 6,558,910 | B2 | 5/2003 | Zuker et al. |
| 2003/0232325 | A1 | 12/2003 | Palese et al. |
| 2004/0265230 | A1 | 12/2004 | Martinez et al. |
| 2005/0079485 | A1 | 4/2005 | Schultz-Cherry et al. |
| 2005/0100885 | A1 | 5/2005 | Crooke et al. |

FOREIGN PATENT DOCUMENTS

| CN | 1 539 967 A | 10/2004 |
|---|---|---|
| WO | WO 9426902 A1 * | 11/1994 |
| WO | WO 2004/096842 A2 | 11/2004 |
| WO | WO 2007130519 A2 * | 11/2007 |

OTHER PUBLICATIONS

PCT/US 10/45928 International Search Report, Jan. 26, 2011, Blood System, Inc.
Kapoor et al., "Multiple novel astrovirus species in human stool", J. Gen Virol.; vol. 90 (Pt 12) p. 2965-2972 Epub Aug. 19, 2009.
Sakamoto, "Molecular epidemiology of astroviruses in Japan from 1995 to 1998 by reverse transcription-polymerase chain reaction with serotype-specific primers(1 to 8)", J. Med Virol. vol. 61(3) p. 326-331; Abstract Only; 2000.
Finkbeiner et al., "Identification of a novel astrovirus (astrovirus VA1) associated with an outbreak of acute gastroenteritis", *J. Virol.*, 83(20):10836-9 (2009).
Sakamoto et al., "Molecular epidemiology of astroviruses in Japan from 1995 to 1998 by reverse transcription-polymerase chain reaction with serotype-specific primers (1 to 8)", *J. Med. Virol.*, 61(3):326-31 (2000).
Zhu et al., "Detection of diverse astroviruses from bats in China", *J. Gen. Viral.*, 90(Pt 4):883-887 (2009).
Supplementary European Search Report (ESR) from EP 10 81 0561.

* cited by examiner

*Primary Examiner* — Louise Humphrey
(74) *Attorney, Agent, or Firm* — DLA Piper LLP (US)

(57) ABSTRACT

Provided herein are sequences of the genomes and encoded proteins of new astrovirus species, and variants thereof. Also provided are methods of detecting the new astrovirus species and diagnosing astrovirus infection, methods of treating or preventing astrovirus infection, and methods for identifying anti-astrovirus compounds.
Provided are two new astrovirus species named HMOAstV-A and HMOAstV-B, and both are distantly related to known astroviruses. Also provided is a new method of classifying astroviruses, where there are three groups of human astroviruses, including HAstV, AstV-MLB, and HMOAstV.

8 Claims, 4 Drawing Sheets

SEQUENCE LISTING

<160> NUMBER OF SEQ ID NOS: 21

<210> SEQ ID NO 1
<211> LENGTH: 6534
<212> TYPE: DNA
<213> ORGANISM: Astrovirus

<400> SEQUENCE: 1

```
ccaagtaggg tttggtgcct ttgggcatct ggtgggttag ctatggagcg ttcctataaa      60 ccaagggtc  ttaatatcta tgacccttat gaccgtgttt tgcaacacgg gagtaagagt     120
```

```
gccagaataa aagggattca actggacaag gtttcaggga ataagttggc agacatattc    180
tcagatggtg gcccattgtg ttttggttat ggagttctgg aaatggttaa ggttgatact    240
ggttcagtgc agccagtaac tacaccagta aaaaccgtgt acgtctcagg tgtccttgcg    300
ggcaatgagt acgttaccta ctgcttcaaa cctggtgtta accagtgggt tgaagtggat    360
ccagatatac atcaaccaac ggctttggtg ggtacactgt atcaggaata caaaaagctg    420
gtccagtctg aaagggaatt gaaagaaact aagtcaggac tacaattaga aatatccctt    480
ttaaggcatg aattggaacg ctccagaccc actgttagaa ccctacgccc atacaaaatg    540
gctaacatag tgttttttgg attgctattg ggattgttaa tggcacatgc agtcacaggt    600
tttagaacag gacaatgcct tgattcagat gtaagtgaaa cattgaagcc ccagacctgt    660
attaactgga aatgggatgg tggtatagct ccagataccg aggtaccact ggttgagagg    720
gcatatgcat ggtacatagg agttaaacag cagatgaagg aatactataa tgatagtgtt    780
atagtagagt ggtctgtgta tgtgttcaaa atgttatgtt catggacatc agttgcagtg    840
accatagggg ttttctatat gatcaaatca gagaatccca tgtatatgat gttaacacta    900
atgctggcta cactatcaag gatacagcta atggcagttg ctgccatacc tggaatggaa    960
ataacatcaa cattttcatt gtggtgctgt atgatagtgt actactttaa tcaagcagct   1020
gcgatggcat ctgcaattta ttatagcttt cagtgtgtta tgtcctcctg catgttcatg   1080
agtgacattg aatatgtaca agttttgaga ggccatgcag tggttgtttt taccataatt   1140
tgttcccata ttttccatat tttacaaata ccatcctggg ttactgtttt aataatggtt   1200
ctatataggg tggtaaggct aactagtgtt gtgattgggg agaaaattga ggttaggaac   1260
ctcgatggta aggtggttaa tacaatcaca acacagacat catggcttaa taaagtctcc   1320
aaatttgtgc aaagcaaatt taaacaaaat gttagggtgg gtgtttcatc aactgctcga   1380
gttgtaccaa atggggtatt agttgtggag gccaaggata acattgggac tggctttaga   1440 gtgcaaaaact atgttgttac agcagcacac gttgttggta gtgaaaccca ggttcgccta   1500
aaatggggtg atgttagtgc atttgctaag gttgtttata tacatcctag caaggatgtg   1560
gcatatttaa gtttgccacc tgaaatgcag aacctaccaa cgtacaagtt tgcaaaagcc   1620
gtcgctgatg ggactatagt cattacctca ttagaggatt gtgggggtttt ggctgttgcc   1680 atcacagaag gtgttgtcgt ctctaacaac atgacatatg ctgtgtgtac taaaaatggc   1740
atgagtgggt caccagttac caatgttgat gggcgcgtta ttggtgttca tcagacaaac   1800
actgggttta ctggtggtgc agtcattata cgccaggaag acctcccacc ccaaaagaag   1860
ccacaacgtg agttggagct ggaggagaag gttaaacaac ttgaggaagc cttagcagga   1920
aaaatgaacc aaaaattcag tgaagaccag gtcatcgaat tgataaggat ggccgttggt   1980
agagaaattg gaatattacg ccatgaattg tctatgaatc aagccaaagg taaaaataag   2040
ggcaagaagc gtggcaatgt caaacgtaag aggaggagga tgtggactga agaagagtac   2100
aaagagcttc tagaaaaagg cttcaccaga cagcagctgc gggatatggc tgagacgctg   2160
cgtgaggcag aatacactga cactgagagt gaggaatatg aatcaggtta tcctgcttgg   2220
tctgatccag aagattctga tgagatagat cgagaatggt ttggacctaa aagaagata    2280 cttgatgagg ttgattctgg atggtccaaa ggagacttct gggaacagtg tcaaaaagtg   2340
tggaaggaaa ctgaaccgat gagtgaggag caagtaaata ctcttccatc acacctacat   2400
gagaagtatg gtttgacatg ttacgttatc acaaaagcag acatggaggc attggctaaa   2460
gatttgctaa agtatcaatc attggttgaa gataaaataa agaacaatgt ggtcaggggc   2520
```

```
caatggattg atggtgtgga tcccaaggtg attataaatg aattggatga actgtggctt    2580
ggtatcaatc acataatgtg ggagaatgga cttgtcccat ttacccaacg ccgcaaggtc    2640
aataagagaa agaatcaaaa aacttgaaag gggggctca aggtgagccc ccaacaaaag     2700
aacaattaac tctttcttat tgggaaaata tgttggagcc aggggactat tatctcaccc    2760
ctccaacata ccctttattg ggtattttac caattaatcg accaatatgt gattatgatg    2820
agccaattga tgatttgcta aatttgttgc caagttatga tgatgatatg tcatatggtc    2880
caacaatttg gggccctgaa gcctatgtca agtcatttga aaagtttaca tataaggaac    2940
caatgagtaa catcaaggac aaatataaga gagagtggaa ttttgccatg agagtcttga    3000
ggagggaatt tgattaccta gttgatagtg tgatgacaga catcacagca acatctaaga    3060
attcagactc cacaccctcc tatccaaaat gcctgtggtg aaaacagag gctgaatact     3120
taaaggacag aggttaccaa gattacataa cacagctgga atccataaag aaaggtgaaa    3180
ggcccagagt cctctggtat tgttcctca agaaagaaat cctaaagctt agcaaaattg     3240
aggatgggga tatacgacaa atcgtgtgtt cagatccgat attttgcgcgc attgggtgtg   3300
tttttgagga acatcagaac aacctaatga agatgaggac aaagacccgc atggggcaat   3360
gtggctggtc cccattctgt ggtggcttca atgatcgtgt caagagattg gtggataaag    3420
gcaacaatct gtttgttgag tttgattgga cacgatgatg tggtacaata ccgaatgaag    3480
tgtttatggc aattaaacag tttaggtact catgtttagc tgaggagttt aagacagagg    3540
aaaacttgag tatctacaaa tggtattgtg agagtatact agataggtac gtcatgttac    3600
cttctggcga agtcaccaaa caggttaggg ggaacccttc aggtcaggtg tcaacaacta    3660
tggacaataa cttgtgtaat gtcttcttcc aagcgtttga atacgcgtac atgcatcctg    3720
ataaggatat aagtcaactt atgcatgact gggagaaggt tgattcactt atttatggtg    3780
atgataggtt gtctacttat cctgagctgc ctgaagatta tgtagacaga gttgttgaca    3840
tgtacgccac agtgtttgga atgtgggtca aacctgaaaa agtgaaaatc tcaaacagta    3900
taataggcct tacattttgt ggttttacag tgacagaatc aaatgggatt tatgtcccag    3960
tccccacaga aacagagaaa ctcatggctg gactagtgcg accaactaaa agattacccg    4020
acattttatc gctgtatggg aaactccttt gctaccgcat actaagtcac aatctgccag    4080
atgaccacaa atttaaaaat tacatcttgg tggccttaga agttgtggct aggcacatcc    4140
gtgctagtgg aggtgaagag ccttactata ttacggatgg tatgctggat agactttgga    4200
ggggcggacc aaaagcgtgga gatggctggt aagcagcccc agcatgctgc aactaaggct    4260
gccattaagg cagttgctaa agaggttgtc aaggaggaga agaaagcatt caaacccaga    4320
cagcaaaata aaagcactag gaataagttt agaaatataat ggcaaactaa acatcaagtt    4380
aagaatgaaa ttaagactga acttaagaag aaaggacttg agggacccaa gacaaaattt    4440
acagttaagg tctcagcaac aatcggaaaa attggaccaa atgtaaattc agggcctgaa    4500
ttacaaattt caacatttat gcatcctgct ttaatgaaag agccaaatga tggcaccaat    4560
tttggcccat tgcaagctgc agccgctcag tggggttttgt ggagactatc agacctcaag   4620
atacaattta caccactcgt gggttcatcg gctgtaaccg gctcagtgta ccgcacatct    4680
ttgaacctaa cgcaatcccc tggatccaca tcttgggtg gcttaggtgc ccggaaacac     4740
ctggatatcc cagttggggt gtcacggaca tggcacttaa ggaaaggtga ccttgcggga    4800
cccagagaga catggtggtt aacagacacc aatgaagagg gaggacaaag ttgcggtccc    4860
atgcttgaag tccatggcct cggtaaaaca acctcaactt ataaggatga agcctggaga    4920
```

```
ggtgatctct ttatagttga ggttacagga gtatggcagt ttacaaacta taatgccaag    4980
cctgctttgg gaacactgaa cagggtggtt gaggacacca cagcgactat tgaggtcggt    5040
acagatggca taatgaagat gtcaatacca tctactgggc agctagcacg ccacatgtca    5100
gagcaaaatg aaagggcatc aaatgcagcg aacacaattg gtgagaccat atggcaggtt    5160
gttgaccaag gagctggtct tgttgctagt gttgcacctg agccttttgg ctggctcatc    5220
aagggtggtt ggtggtttgt caagaaactg attggtaggg ctaacaccac cactgaacaa    5280
tactatgttt atgcttcact agcagatgca caaaacaaca aaccagttga agcaaatacc    5340
tttgctgctt caagccatgc tacaacactg gctgttactc agataaatgc ccctaacact    5400
gggccaagca cagcctcagc ggttgtccaa tccagaatgt ttcccctacc acaagcgggg    5460
attcccgatg gttggttttg gctcagtggg caatttgaag ctttgcatat ggttggtcta    5520
aatggcacca acggatctgc tcttccatgt ggtatgatta catcatttga caaatgggag    5580
ttcaaactaa agaaaggcac tgttgagtgg ggatgtgcta tgcaaggaat ggcagcagca    5640
agcaacactg ttacttgctg gtcagttgat cgtgaaaatc agcttttggg ttggtacgat    5700
gtcagcggca ttgcttcaac tggcattgtt gttgattggg tgactggccc aaatggtggc    5760
actgtgcatt tggattgggc cgatgtcctt gcttggagga cagatttgtg ggggacactc    5820
cgcatgacat actggttgtg tcgaactaga agagccgtgc aaggctctga ctttgacaca    5880
acacagaaga gcccgtcgcc ttatatcgcg cgggcttggc ctgagacaat aagtaatgtc    5940
aggcttgatg ttcgggaggt tttgatggtc aatacaacca ccaatgctac cgattcaaat    6000
agccgagtcc aatatatcca aagagtgcca gctggcgcca tagtcatact ctggtgcctt    6060
gggaatcaca catttgacac atcaactggc caaggttcca ttgtccaaaa gtcctcattt    6120
ggtggatttg gacagctgcc tagtaagtca tctactactg gtttgtggtc tcgtgcactt    6180
aattcagttg gtccatccac cgattggatt actgtgtctt ttgactcaca tccaccagtt    6240
tgtgatgatg ttgtttcaag gctgatggct gaaattgctg acaggtatga ccttgagccc    6300
cgcagaaaga agcctaagga tgcaaccaaa gagctaacca ggctcaaaat ctatgaagca    6360
cttagagaag ctgattggga acacctgcct gcagaggagg tgagctcagt gctttgaatt    6420
ccgccgaggc cacgccgagt aggatcgagg gtacagcgga ctattgattg cttgtggaat    6480
gaattagttt atgattataa tctgttcatt tgatcattag tgaatttgat tctc           6534
```

<210> SEQ ID NO 2
<211> LENGTH: 874
<212> TYPE: PRT
<213> ORGANISM: Astrovirus

<400> SEQUENCE: 2

```
Met Glu Arg Ser Tyr Lys Pro Arg Gly Leu Asn Ile Tyr Asp Pro Tyr
1               5                   10                  15

Asp Arg Val Leu Gln His Gly Ser Lys Ser Ala Arg Ile Lys Gly Ile
            20                  25                  30

Gln Leu Asp Lys Val Ser Gly Asn Lys Leu Ala Asp Ile Phe Ser Asp
        35                  40                  45

Gly Gly Pro Leu Cys Phe Gly Tyr Gly Val Leu Glu Met Val Lys Val
    50                  55                  60

Asp Thr Gly Ser Val Gln Pro Val Thr Thr Pro Val Lys Thr Val Tyr
65                  70                  75                  80

Val Ser Gly Val Leu Ala Gly Asn Glu Tyr Val Thr Tyr Cys Phe Lys
                85                  90                  95
```

-continued

Pro Gly Val Asn Gln Trp Val Glu Val Asp Pro Asp Ile His Gln Pro
            100                 105                 110

Thr Ala Leu Val Gly Thr Leu Tyr Gln Glu Tyr Lys Lys Leu Val Gln
        115                 120                 125

Ser Glu Arg Glu Leu Lys Glu Thr Lys Ser Gly Leu Gln Leu Glu Ile
    130                 135                 140

Ser Leu Leu Arg His Glu Leu Glu Arg Ser Arg Pro Thr Val Arg Thr
145                 150                 155                 160

Leu Arg Pro Tyr Lys Met Ala Asn Ile Val Phe Phe Gly Leu Leu Leu
                165                 170                 175

Gly Leu Leu Met Ala His Ala Val Thr Gly Phe Arg Thr Gly Gln Cys
            180                 185                 190

Leu Asp Ser Asp Val Ser Glu Thr Leu Lys Pro Gln Thr Cys Ile Asn
        195                 200                 205

Trp Lys Trp Asp Gly Gly Ile Ala Pro Asp Thr Glu Val Pro Leu Val
    210                 215                 220

Glu Arg Ala Tyr Ala Trp Tyr Ile Gly Val Lys Gln Gln Met Lys Glu
225                 230                 235                 240

Tyr Tyr Asn Asp Ser Val Ile Val Glu Trp Ser Val Tyr Val Phe Lys
                245                 250                 255

Met Leu Cys Ser Trp Thr Ser Val Ala Val Thr Ile Gly Val Phe Tyr
            260                 265                 270

Met Ile Lys Ser Glu Asn Pro Met Tyr Met Met Leu Thr Leu Met Leu
        275                 280                 285

Ala Thr Leu Ser Arg Ile Gln Leu Met Ala Val Ala Ala Ile Pro Gly
290                 295                 300

Met Glu Ile Thr Ser Thr Phe Ser Leu Trp Cys Cys Met Ile Val Tyr
305                 310                 315                 320

Tyr Phe Asn Gln Ala Ala Ala Met Ala Ser Ala Ile Tyr Tyr Ser Phe
                325                 330                 335

Gln Cys Val Met Ser Ser Cys Met Phe Met Ser Asp Ile Glu Tyr Val
            340                 345                 350

Gln Val Leu Arg Gly His Ala Val Val Phe Thr Ile Ile Cys Ser
        355                 360                 365

His Ile Phe His Ile Leu Gln Ile Pro Ser Trp Val Thr Val Leu Ile
    370                 375                 380

Met Val Leu Tyr Arg Val Val Arg Leu Thr Ser Val Val Ile Gly Glu
385                 390                 395                 400

Lys Ile Glu Val Arg Asn Leu Asp Gly Lys Val Val Asn Thr Ile Thr
                405                 410                 415

Thr Gln Thr Ser Trp Leu Asn Lys Val Ser Lys Phe Val Gln Ser Lys
            420                 425                 430

Phe Lys Gln Asn Val Arg Val Gly Val Ser Ser Thr Ala Arg Val Val
        435                 440                 445

Pro Asn Gly Val Leu Val Val Glu Ala Lys Asp Asn Ile Gly Thr Gly
    450                 455                 460

Phe Arg Val Gln Asn Tyr Val Val Thr Ala Ala His Val Val Gly Ser
465                 470                 475                 480

Glu Thr Gln Val Arg Leu Lys Trp Gly Asp Val Ser Ala Phe Ala Lys
                485                 490                 495

Val Val Tyr Ile His Pro Ser Lys Asp Val Ala Tyr Leu Ser Leu Pro
            500                 505                 510

Pro Glu Met Gln Asn Leu Pro Thr Tyr Lys Phe Ala Lys Ala Val Ala

```
               515                 520                 525
Asp Gly Thr Ile Val Ile Thr Ser Leu Glu Asp Cys Gly Val Leu Ala
            530                 535                 540
Val Ala Ile Thr Glu Gly Val Val Ser Asn Asn Met Thr Tyr Ala
545                 550                 555                 560
Val Cys Thr Lys Asn Gly Met Ser Gly Ser Pro Val Thr Asn Val Asp
                565                 570                 575
Gly Arg Val Ile Gly Val His Gln Thr Asn Thr Gly Phe Thr Gly Gly
            580                 585                 590
Ala Val Ile Ile Arg Gln Glu Asp Leu Pro Pro Gln Lys Lys Pro Gln
        595                 600                 605
Arg Glu Leu Glu Leu Glu Glu Lys Val Lys Gln Leu Glu Glu Ala Leu
    610                 615                 620
Ala Gly Lys Met Asn Gln Lys Phe Ser Glu Asp Gln Val Ile Glu Leu
625                 630                 635                 640
Ile Arg Met Ala Val Gly Arg Glu Ile Gly Ile Leu Arg His Glu Leu
                645                 650                 655
Ser Met Asn Gln Ala Lys Gly Lys Asn Lys Gly Lys Lys Arg Gly Asn
            660                 665                 670
Val Lys Arg Lys Arg Arg Met Trp Thr Glu Glu Glu Tyr Lys Glu
        675                 680                 685
Leu Leu Glu Lys Gly Phe Thr Arg Gln Gln Leu Arg Asp Met Ala Glu
    690                 695                 700
Thr Leu Arg Glu Ala Glu Tyr Thr Asp Thr Glu Ser Glu Glu Tyr Glu
705                 710                 715                 720
Ser Gly Tyr Pro Ala Trp Ser Asp Pro Glu Asp Ser Asp Glu Ile Asp
                725                 730                 735
Arg Glu Trp Phe Gly Pro Lys Lys Lys Ile Leu Asp Glu Val Asp Ser
            740                 745                 750
Gly Trp Ser Lys Gly Asp Phe Trp Glu Gln Cys Gln Lys Val Trp Lys
        755                 760                 765
Glu Thr Glu Pro Met Ser Glu Glu Gln Val Asn Thr Leu Pro Ser His
    770                 775                 780
Leu His Glu Lys Tyr Gly Leu Thr Cys Tyr Val Ile Thr Lys Ala Asp
785                 790                 795                 800
Met Glu Ala Leu Ala Lys Asp Leu Leu Lys Tyr Gln Ser Leu Val Glu
                805                 810                 815
Asp Lys Ile Lys Asn Asn Val Arg Gly Gln Trp Ile Asp Gly Val
            820                 825                 830
Asp Pro Lys Val Ile Ile Asn Glu Leu Asp Glu Leu Trp Leu Gly Ile
        835                 840                 845
Asn His Ile Met Trp Glu Asn Gly Leu Val Pro Phe Thr Gln Arg Arg
    850                 855                 860
Lys Val Asn Lys Arg Lys Asn Gln Lys Thr
865                 870

<210> SEQ ID NO 3
<211> LENGTH: 1395
<212> TYPE: PRT
<213> ORGANISM: Astrovirus

<400> SEQUENCE: 3

Met Glu Arg Ser Tyr Lys Pro Arg Gly Leu Asn Ile Tyr Asp Pro Tyr
1               5                   10                  15
Asp Arg Val Leu Gln His Gly Ser Lys Ser Ala Arg Ile Lys Gly Ile
```

```
                    20                  25                  30
Gln Leu Asp Lys Val Ser Gly Asn Lys Leu Ala Asp Ile Phe Ser Asp
                35                  40                  45

Gly Gly Pro Leu Cys Phe Gly Tyr Gly Val Leu Glu Met Val Lys Val
            50                  55                  60

Asp Thr Gly Ser Val Gln Pro Val Thr Thr Pro Val Lys Thr Val Tyr
65                  70                  75                  80

Val Ser Gly Val Leu Ala Gly Asn Glu Tyr Val Thr Tyr Cys Phe Lys
                85                  90                  95

Pro Gly Val Asn Gln Trp Val Glu Val Asp Pro Asp Ile His Gln Pro
            100                 105                 110

Thr Ala Leu Val Gly Thr Leu Tyr Gln Glu Tyr Lys Lys Leu Val Gln
        115                 120                 125

Ser Glu Arg Glu Leu Lys Glu Thr Lys Ser Gly Leu Gln Leu Glu Ile
    130                 135                 140

Ser Leu Leu Arg His Glu Leu Glu Arg Ser Arg Pro Thr Val Arg Thr
145                 150                 155                 160

Leu Arg Pro Tyr Lys Met Ala Asn Ile Val Phe Phe Gly Leu Leu
                165                 170                 175

Gly Leu Leu Met Ala His Ala Val Thr Gly Phe Arg Thr Gly Gln Cys
            180                 185                 190

Leu Asp Ser Asp Val Ser Glu Thr Leu Lys Pro Gln Thr Cys Ile Asn
        195                 200                 205

Trp Lys Trp Asp Gly Gly Ile Ala Pro Asp Thr Glu Val Pro Leu Val
    210                 215                 220

Glu Arg Ala Tyr Ala Trp Tyr Ile Gly Val Lys Gln Gln Met Lys Glu
225                 230                 235                 240

Tyr Tyr Asn Asp Ser Val Ile Val Glu Trp Ser Val Tyr Val Phe Lys
                245                 250                 255

Met Leu Cys Ser Trp Thr Ser Val Ala Val Thr Ile Gly Val Phe Tyr
            260                 265                 270

Met Ile Lys Ser Glu Asn Pro Met Tyr Met Met Leu Thr Leu Met Leu
        275                 280                 285

Ala Thr Leu Ser Arg Ile Gln Leu Met Ala Val Ala Ala Ile Pro Gly
    290                 295                 300

Met Glu Ile Thr Ser Thr Phe Ser Leu Trp Cys Cys Met Ile Val Tyr
305                 310                 315                 320

Tyr Phe Asn Gln Ala Ala Ala Met Ala Ser Ala Ile Tyr Tyr Ser Phe
                325                 330                 335

Gln Cys Val Met Ser Ser Cys Met Phe Met Ser Asp Ile Glu Tyr Val
            340                 345                 350

Gln Val Leu Arg Gly His Ala Val Val Val Phe Thr Ile Ile Cys Ser
        355                 360                 365

His Ile Phe His Ile Leu Gln Ile Pro Ser Trp Val Thr Val Leu Ile
    370                 375                 380

Met Val Leu Tyr Arg Val Val Arg Leu Thr Ser Val Val Ile Gly Glu
385                 390                 395                 400

Lys Ile Glu Val Arg Asn Leu Asp Gly Lys Val Val Asn Thr Ile Thr
                405                 410                 415

Thr Gln Thr Ser Trp Leu Asn Lys Val Ser Lys Phe Val Gln Ser Lys
            420                 425                 430

Phe Lys Gln Asn Val Arg Val Gly Val Ser Ser Thr Ala Arg Val Val
        435                 440                 445
```

-continued

```
Pro Asn Gly Val Leu Val Glu Ala Lys Asp Asn Ile Gly Thr Gly
450                 455                 460

Phe Arg Val Gln Asn Tyr Val Thr Ala His Val Val Gly Ser
465                 470                 475                 480

Glu Thr Gln Val Arg Leu Lys Trp Gly Asp Val Ser Ala Phe Ala Lys
                    485                 490                 495

Val Val Tyr Ile His Pro Ser Lys Asp Val Ala Tyr Leu Ser Leu Pro
                500                 505                 510

Pro Glu Met Gln Asn Leu Pro Thr Tyr Lys Phe Ala Lys Ala Val Ala
            515                 520                 525

Asp Gly Thr Ile Val Ile Thr Ser Leu Glu Asp Cys Gly Val Leu Ala
        530                 535                 540

Val Ala Ile Thr Glu Gly Val Val Ser Asn Asn Met Thr Tyr Ala
545                 550                 555                 560

Val Cys Thr Lys Asn Gly Met Ser Gly Ser Pro Val Thr Asn Val Asp
                565                 570                 575

Gly Arg Val Ile Gly Val His Gln Thr Asn Thr Gly Phe Thr Gly Gly
                580                 585                 590

Ala Val Ile Ile Arg Gln Glu Asp Leu Pro Pro Gln Lys Lys Pro Gln
        595                 600                 605

Arg Glu Leu Glu Leu Glu Glu Lys Val Lys Gln Leu Glu Glu Ala Leu
    610                 615                 620

Ala Gly Lys Met Asn Gln Lys Phe Ser Glu Asp Gln Val Ile Glu Leu
625                 630                 635                 640

Ile Arg Met Ala Val Gly Arg Glu Ile Gly Ile Leu Arg His Glu Leu
                645                 650                 655

Ser Met Asn Gln Ala Lys Gly Lys Asn Lys Gly Lys Lys Arg Gly Asn
                660                 665                 670

Val Lys Arg Lys Arg Arg Arg Met Trp Thr Glu Glu Tyr Lys Glu
    675                 680                 685

Leu Leu Glu Lys Gly Phe Thr Arg Gln Gln Leu Arg Asp Met Ala Glu
    690                 695                 700

Thr Leu Arg Glu Ala Glu Tyr Thr Asp Thr Glu Ser Glu Glu Tyr Glu
705                 710                 715                 720

Ser Gly Tyr Pro Ala Trp Ser Asp Pro Glu Asp Ser Asp Glu Ile Asp
                725                 730                 735

Arg Glu Trp Phe Gly Pro Lys Lys Ile Leu Asp Glu Val Asp Ser
                740                 745                 750

Gly Trp Ser Lys Gly Asp Phe Trp Glu Gln Cys Gln Lys Val Trp Lys
                755                 760                 765

Glu Thr Glu Pro Met Ser Glu Glu Gln Val Asn Thr Leu Pro Ser His
    770                 775                 780

Leu His Glu Lys Tyr Gly Leu Thr Cys Tyr Val Ile Thr Lys Ala Asp
785                 790                 795                 800

Met Glu Ala Leu Ala Lys Asp Leu Leu Lys Tyr Gln Ser Leu Val Glu
                805                 810                 815

Asp Lys Ile Lys Asn Asn Val Val Arg Gly Gln Trp Ile Asp Gly Val
                820                 825                 830

Asp Pro Lys Val Ile Ile Asn Glu Leu Asp Glu Leu Trp Leu Gly Ile
        835                 840                 845

Asn His Ile Met Trp Glu Asn Gly Leu Val Pro Phe Thr Gln Arg Arg
    850                 855                 860

Lys Val Asn Lys Arg Lys Asn Gln Asn Leu Lys Gly Gly Ala Gln Gly
865                 870                 875                 880
```

```
Glu Pro Pro Thr Lys Glu Gln Leu Thr Leu Ser Tyr Trp Glu Asn Met
                885                 890                 895
Leu Glu Pro Gly Asp Tyr Tyr Leu Thr Pro Thr Tyr Pro Leu Leu
            900                 905                 910
Gly Ile Leu Pro Ile Asn Arg Pro Ile Cys Asp Tyr Asp Glu Pro Ile
                915                 920                 925
Asp Asp Leu Leu Asn Leu Leu Pro Ser Tyr Asp Asp Met Ser Tyr
    930                 935                 940
Gly Pro Thr Ile Trp Gly Pro Glu Ala Tyr Val Lys Ser Phe Glu Lys
945                 950                 955                 960
Phe Thr Tyr Lys Glu Pro Met Ser Asn Ile Lys Asp Lys Tyr Lys Arg
                965                 970                 975
Glu Trp Asn Phe Ala Met Arg Val Leu Arg Arg Glu Phe Asp Tyr Leu
                980                 985                 990
Val Asp Ser Val Met Thr Asp Ile Thr Ala Thr Ser Lys Asn Ser Asp
            995                 1000                1005
Ser Thr Pro Ser Tyr Pro Lys Cys Leu Trp Trp Lys Thr Glu Ala
    1010                1015                1020
Glu Tyr Leu Lys Asp Arg Gly Tyr Gln Asp Tyr Ile Thr Gln Leu
    1025                1030                1035
Glu Ser Ile Lys Lys Gly Glu Arg Pro Arg Val Leu Trp Tyr Leu
    1040                1045                1050
Phe Leu Lys Lys Glu Ile Leu Lys Leu Ser Lys Ile Glu Asp Gly
    1055                1060                1065
Asp Ile Arg Gln Ile Val Cys Ser Asp Pro Ile Phe Ala Arg Ile
    1070                1075                1080
Gly Cys Val Phe Glu Glu His Gln Asn Asn Leu Met Lys Met Arg
    1085                1090                1095
Thr Lys Thr Arg Met Gly Gln Cys Gly Trp Ser Pro Phe Cys Gly
    1100                1105                1110
Gly Phe Asn Asp Arg Val Lys Arg Leu Val Asp Lys Gly Asn Asn
    1115                1120                1125
Leu Phe Val Glu Phe Asp Trp Thr Arg Tyr Asp Gly Thr Ile Pro
    1130                1135                1140
Asn Glu Val Phe Met Ala Ile Lys Gln Phe Arg Tyr Ser Cys Leu
    1145                1150                1155
Ala Glu Glu Phe Lys Thr Glu Glu Asn Leu Ser Ile Tyr Lys Trp
    1160                1165                1170
Tyr Cys Glu Ser Ile Leu Asp Arg Tyr Val Met Leu Pro Ser Gly
    1175                1180                1185
Glu Val Thr Lys Gln Val Arg Gly Asn Pro Ser Gly Gln Val Ser
    1190                1195                1200
Thr Thr Met Asp Asn Asn Leu Cys Asn Val Phe Phe Gln Ala Phe
    1205                1210                1215
Glu Tyr Ala Tyr Met His Pro Asp Lys Asp Ile Ser Gln Leu Met
    1220                1225                1230
His Asp Trp Glu Lys Val Asp Ser Leu Ile Tyr Gly Asp Asp Arg
    1235                1240                1245
Leu Ser Thr Tyr Pro Glu Leu Pro Glu Asp Tyr Val Asp Arg Val
    1250                1255                1260
Val Asp Met Tyr Ala Thr Val Phe Gly Met Trp Val Lys Pro Glu
    1265                1270                1275
Lys Val Lys Ile Ser Asn Ser Ile Ile Gly Leu Thr Phe Cys Gly
```

```
                1280              1285              1290
Phe Thr Val Thr Glu Ser Asn Gly Ile Tyr Val Pro Val Pro Thr
    1295              1300              1305

Glu Thr Glu Lys Leu Met Ala Gly Leu Val Arg Pro Thr Lys Arg
    1310              1315              1320

Leu Pro Asp Ile Leu Ser Leu Tyr Gly Lys Leu Leu Cys Tyr Arg
    1325              1330              1335

Ile Leu Ser His Asn Leu Pro Asp Asp His Lys Phe Lys Asn Tyr
    1340              1345              1350

Ile Leu Val Ala Leu Glu Val Val Ala Arg His Ile Arg Ala Ser
    1355              1360              1365

Gly Gly Glu Glu Pro Tyr Tyr Ile Thr Asp Gly Met Leu Asp Arg
    1370              1375              1380

Leu Trp Arg Gly Gly Pro Lys Arg Gly Asp Gly Trp
    1385              1390              1395

<210> SEQ ID NO 4
<211> LENGTH: 731
<212> TYPE: PRT
<213> ORGANISM: Astrovirus

<400> SEQUENCE: 4

Met Ala Gly Lys Gln Pro Gln His Ala Ala Thr Lys Ala Ala Ile Lys
1               5                   10                  15

Ala Val Ala Lys Glu Val Val Lys Glu Glu Lys Lys Ala Phe Lys Pro
                20                  25                  30

Arg Gln Gln Asn Lys Ser Thr Arg Asn Lys Phe Arg Asn Lys Trp Gln
            35                  40                  45

Thr Lys His Gln Val Lys Asn Glu Ile Lys Thr Glu Leu Lys Lys Lys
        50                  55                  60

Gly Leu Glu Gly Pro Lys Thr Lys Phe Thr Val Lys Val Ser Ala Thr
65                  70                  75                  80

Ile Gly Lys Ile Gly Pro Asn Val Asn Ser Gly Pro Glu Leu Gln Ile
                85                  90                  95

Ser Thr Phe Met His Pro Ala Leu Met Lys Glu Pro Asn Asp Gly Thr
            100                 105                 110

Asn Phe Gly Pro Leu Gln Ala Ala Ala Gln Trp Gly Leu Trp Arg
            115                 120                 125

Leu Ser Asp Leu Lys Ile Gln Phe Thr Pro Leu Val Gly Ser Ser Ala
    130                 135                 140

Val Thr Gly Ser Val Tyr Arg Thr Ser Leu Asn Leu Thr Gln Ser Pro
145                 150                 155                 160

Gly Ser Thr Ser Trp Gly Gly Leu Gly Ala Arg Lys His Leu Asp Ile
                165                 170                 175

Pro Val Gly Val Ser Arg Thr Trp His Leu Arg Lys Gly Asp Leu Ala
            180                 185                 190

Gly Pro Arg Glu Thr Trp Trp Leu Thr Asp Thr Asn Glu Glu Gly Gly
        195                 200                 205

Gln Ser Cys Gly Pro Met Leu Glu Val His Gly Leu Gly Lys Thr Thr
    210                 215                 220

Ser Thr Tyr Lys Asp Glu Ala Trp Arg Gly Asp Leu Phe Ile Val Glu
225                 230                 235                 240

Val Thr Gly Val Trp Gln Phe Thr Asn Tyr Asn Ala Lys Pro Ala Leu
                245                 250                 255

Gly Thr Leu Asn Arg Val Val Glu Asp Thr Thr Ala Thr Ile Glu Val
```

-continued

```
                260                 265                 270
Gly Thr Asp Gly Ile Met Lys Met Ser Ile Pro Ser Thr Gly Gln Leu
            275                 280                 285

Ala Arg His Met Ser Glu Gln Asn Glu Arg Ala Ser Asn Ala Ala Asn
        290                 295                 300

Thr Ile Gly Glu Thr Ile Trp Gln Val Val Asp Gln Gly Ala Gly Leu
305                 310                 315                 320

Val Ala Ser Val Ala Pro Glu Pro Phe Gly Trp Leu Ile Lys Gly Gly
            325                 330                 335

Trp Trp Phe Val Lys Lys Leu Ile Gly Arg Ala Asn Thr Thr Thr Glu
        340                 345                 350

Gln Tyr Tyr Val Tyr Ala Ser Leu Ala Asp Ala Gln Asn Asn Lys Pro
            355                 360                 365

Val Glu Ala Asn Thr Phe Ala Ala Ser Ser His Ala Thr Leu Ala
        370                 375                 380

Val Thr Gln Ile Asn Ala Pro Asn Thr Gly Pro Ser Thr Ala Ser Ala
385                 390                 395                 400

Val Val Gln Ser Arg Met Phe Pro Leu Pro Gln Ala Gly Ile Pro Asp
            405                 410                 415

Gly Trp Phe Trp Leu Ser Gly Gln Phe Glu Ala Leu His Met Val Gly
            420                 425                 430

Leu Asn Gly Thr Asn Gly Ser Ala Leu Pro Cys Gly Met Ile Thr Ser
        435                 440                 445

Phe Asp Lys Trp Glu Phe Lys Leu Lys Lys Gly Thr Val Glu Trp Gly
        450                 455                 460

Cys Ala Met Gln Gly Met Ala Ala Ala Ser Asn Thr Val Thr Cys Trp
465                 470                 475                 480

Ser Val Asp Arg Glu Asn Gln Leu Leu Gly Trp Tyr Asp Val Ser Gly
            485                 490                 495

Ile Ala Ser Thr Gly Ile Val Val Asp Trp Val Thr Gly Pro Asn Gly
            500                 505                 510

Gly Thr Val His Leu Asp Trp Ala Asp Val Leu Ala Trp Arg Thr Asp
        515                 520                 525

Leu Trp Gly Thr Leu Arg Met Thr Tyr Trp Leu Cys Arg Thr Arg Arg
530                 535                 540

Ala Val Gln Gly Ser Asp Phe Asp Thr Thr Gln Lys Ser Pro Ser Pro
545                 550                 555                 560

Tyr Ile Ala Arg Ala Trp Pro Glu Thr Ile Ser Asn Val Arg Leu Asp
            565                 570                 575

Val Arg Glu Val Leu Met Val Asn Thr Thr Asn Ala Thr Asp Ser
        580                 585                 590

Asn Ser Arg Val Gln Tyr Ile Gln Arg Val Pro Ala Gly Ala Ile Val
        595                 600                 605

Ile Leu Trp Cys Leu Gly Asn His Thr Phe Asp Thr Ser Thr Gly Gln
        610                 615                 620

Gly Ser Ile Val Gln Lys Ser Phe Gly Gly Phe Gly Gln Leu Pro
625                 630                 635                 640

Ser Lys Ser Ser Thr Thr Gly Leu Trp Ser Arg Ala Leu Asn Ser Val
            645                 650                 655

Gly Pro Ser Thr Asp Trp Ile Thr Val Ser Phe Asp Ser His Pro Pro
        660                 665                 670

Val Cys Asp Asp Val Val Ser Arg Leu Met Ala Glu Ile Ala Asp Arg
            675                 680                 685
```

```
Tyr Asp Leu Glu Pro Arg Arg Lys Lys Pro Lys Asp Ala Thr Lys Glu
        690             695             700

Leu Thr Arg Leu Lys Ile Tyr Glu Ala Leu Arg Glu Ala Asp Trp Glu
705             710             715             720

His Leu Pro Ala Glu Glu Val Ser Ser Val Leu
                725             730

<210> SEQ ID NO 5
<211> LENGTH: 5794
<212> TYPE: DNA
<213> ORGANISM: Astrovirus

<400> SEQUENCE: 5
```

| | | | | | |
|---|---|---|---|---|---|
| ctcacagcaa | attaaaagca | tatataacga | ccagttgttc | aactggttgt | tgtatatttc | 60 |
| cactcttaca | tacacatgga | cagctgtggc | attggcaata | ggcacttact | acatgattaa | 120 |
| agctgaaaac | cccatatata | tgctgataac | tttgataatg | ctactatct | caaaaatgca | 180 |
| acttttgcc | gtatcagcta | tacccaatat | ggaaatgact | tcaatgtttt | cattgtggtg | 240 |
| ttgcatggca | ctttacgtgc | taaatcaagc | agcagcaatg | gcagcatccc | ttatgatagc | 300 |
| tatgctatgt | tcagtgattt | gccttttat | gggcgatgct | gaatatatac | aggttatcag | 360 |
| agggcatggt | gttgttatca | tcaccattgt | actgtcacat | gttttccacg | ttttacaaat | 420 |
| accaaattgg | gttactgtct | tggtaatagt | tgcattaagg | attatcaggt | tgatgagtgc | 480 |
| agttattgga | gaaaaaattg | aaatcaggaa | catagatgga | aaagttgtca | atgtgattcc | 540 |
| tacaacaaca | tcatggctta | acagagtttc | tgggtttgtg | cagtccaaat | ttaggcaaaa | 600 |
| agttaggacc | ggtatagttt | caacagctag | agtaattcca | aatggtgttg | tagttgttga | 660 |
| atcaaaggaa | acatcaggta | ccggttttag | agtccaaaat | tacattgtaa | cagcagcaca | 720 |
| tgttgttggt | aatgaaacac | agctcaaagt | taaatgggga | gatgtggtgg | tgtattcaaa | 780 |
| agttgtatat | atccacccaa | ataaagatgt | agcttacatc | acattacccg | ctgagtttca | 840 |
| ggctcttcca | acatataaat | ttgccaaaac | tgttgaggac | ggcactatag | tcattacatc | 900 |
| acttgaagac | tgtggtgttt | tggcagtggc | cgtgtcagag | ggtgttgttg | tcaaagataa | 960 |
| catgacttat | gctattcaaa | ctaagaatgg | aatgagtggt | tctccagtga | caaatgttga | 1020 |
| cggtcgtatt | attggggtac | atcagagtaa | cacaggcttc | acaggaggtg | ctgtcataat | 1080 |
| acgaccagag | gacttgccac | cacaaaagaa | accccagcga | gagttggaat | tggaagcaaa | 1140 |
| aattaaggaa | ttggaagaaa | ctcttaaaag | ccaaatgaac | caggggttga | atgaaaacca | 1200 |
| aatagttgat | ctcattaggt | tagctgttgg | tagggaactt | gaaatcctcc | gccacgaaat | 1260 |
| gaacttgaat | caagcaaaag | gtaagaacaa | gcaccgagga | aaacatggtg | cccgcagacg | 1320 |
| taggaaagtg | cgtgtgtgga | cagaggaaga | atataaagac | ttgcttgaga | aaggattttc | 1380 |
| aagacaacaa | ttacgtgaca | tggctgacgt | gttacgtgag | gctgaataca | ctgatgatga | 1440 |
| cagtgaagac | tttgctgaag | aggaagggta | tcctcagtgg | tctgatcctg | aagactatga | 1500 |
| agaaattgag | agggaatggt | ttggccccaa | gaagaaaatc | ctagatgaag | tggaggatgg | 1560 |
| atggtcaaaa | actgatttct | gggagcagtg | tcaaaaaatt | tggaaagaga | cggaaccaat | 1620 |
| gccagaagaa | tctgttaata | cactaccatc | acatttacat | gataagtatg | cttaacatg | 1680 |
| ttatgtggta | acaaaagctg | atatgcaggc | cttagccaag | gacttgcaag | aataccagca | 1740 |
| aaaagttgag | gacaagatta | aaacaaatgt | tgtccgtggc | cagtgggtca | gtggaattga | 1800 |
| cccaaaggtt | gtgattacag | aattggatga | actctggctt | aagctgaacc | accttatgtg | 1860 |
| gtcacatggt | ttggtcccat | ttatacaaag | aaagaagatc | aataggcgca | agcaacaaaa | 1920 |

```
aaacttgaag ggggccccga agtcggggcc ccaaaaccag accaattaag attggattct   1980
tggaaacaga tgcttgaacc tggtgaatat tttctcactc cagtaaattg ccctttaata   2040
ggtgtcctac caatagatag accaattagt gattatgatg aaccagttga tgatttgttg   2100
aatttattgc ccaaatgtga tgaagatcca ccatatgccc cgtcaacgtg gggcccagaa   2160
gcttatcgta aatcatttca aaaattcttt tataaagaac cagtcaaaaa tataaaagaa   2220
aagtataagc gtgagtggaa gtttgccatg tcagcgctac gtagagaatt tgatttcttg   2280
aatgatagcg tcatgattga cataacagca acatctaaaa atgcagactc cacaccagct   2340
tatcccaaaa ctttatggtg gaaaactgag acagattacc ttaaagatag aggttatcaa   2400
gattatatca ctgagttaga caggataatg gatggagacc gccctgatgt actttggtat   2460
ctcttttttaa agaaagagat tctgaagata agcaagatag aagatgagga catacggcaa   2520
atagtttgtt ctgatcctat atttgctaga ataggctgtg ttttgagga gaatcaaaat   2580
cagctgatga agggcaggac gctgaccaga atgggtcagt gtggttggtc gccattcatg   2640
ggtggcttcc atcgcagggt caaaagatta gtggacaaag gtaataacca ctttatagag   2700
tttgattgga cccgatatga tggcaccatc ccaacagaag ttttttagtgc aatcaaagat   2760
tttaggtttt catgtctcag gaaagaattt agaacagaga agaataaaag tgtttatgac   2820
tggtactgta aaaatatttt taaaaggtat gtcatgttac catctggaga agtcacagtt   2880
caagagcgtg gaaatccttc aggccagata tcaactacca tggataataa tctatgtaat   2940
gtatttttcc aggcatttga gtttgctcat ttgaatccgg ataaaacaat tgatgaactg   3000
agagaaggat gggagaaagt tgattcactt atttatggtg atgataggct ttccacagtt   3060
ccatatgttt gctctaacta tgttgaaaaa gtaatagaca tgtatgaaaa catctttggt   3120
atgtgggtaa aacctaataa agtgaaatta tcagatagtg tgattggcct aacgttttgt   3180
ggttttacca ttacaatgtc agacaatgtt tatgtaccag tcccaacaga tacagacaaa   3240
ttgttagctg gacttgtcac accagtcaag aaattgccag atatttttatc tctctatggg   3300
aagctccttt gctatcgcat ccttggccat aacttgccag acgaccataa gtttaagaac   3360
tacatttttgg tcgctttaga ggtattggct agacacatcc gtaatggtgg tggtgaagaa   3420
ccctatcata ttacggatga gatgctggat agactttgga ggggaggacc aaagttagga   3480
tatggctggt aaacagcccc agcaggccat gcctaaggcc actgtcaagc agttggccaa   3540
ggaagtagtt aagcaggagc gacaggtgaa acagaaccaa ccaaagaaaa agtattttcc   3600
agtgaagaat aaaaagtata taagagggga ggttaggaag gatttaaaga aacaaggctt   3660
tgaaggtcca aaacctagat tctctgtttc agtatcagca acaattggaa aagttgggcc   3720
gaataaggca caggggcccg agttacaaat ttcaactttt atgcatccaa gtcttatgaa   3780
ggagccaaac gacggcacaa atttttggtcc attgcaatca gccgcagccc agtggggact   3840
gtggagactc aaaaatctca gtgtcacatt tacaccattg gttggcccat cagcggtcac   3900
cggctcagtt ttcagaattt cactgaacat ggcacaatcc ccaggtgcta catcttgggg   3960
aggggttgggt gctagaaaac atcgagatgt tgctgttgga aagcagttta catggaaact   4020
ccaacgtggg gatctcactg gacccagaga aacttggtgg cttacagata caaatgaaga   4080
gggagcccaa agctgtgggc ctttgcttga atacatggt cttggagcaa ctacctcaac   4140
ctacaaagat gcagcatgga acggtgacct ttttatagtt gaggtaaaag gtaggtggga   4200
gtttgccaac tataatagca aaccagcatt gggaatgcta gagaggatca ccgagagtac   4260
tagtgcatct atagaagtta ctgatggtaa catgatcatg actgtcccta gaagttctca   4320
```

```
actagctcgc catatgggtg aacgctatga gaagtctgga aatgcatcaa cagtaggtga    4380
gacaatttgg caaatagttg atgagggtgc tggccttgtg gcgaacgttg ccccaccgcc    4440
attcacttgg ttgataaagg gcggttggtg gtttgtcaag aaattgcttg gtagatcagc    4500
aaatactgat gcccagtacc ttgtttatgc gtccttggct gacgcacaga acaaccgacc    4560
agttgaggca cagacattcc cgaagacaac acacacaaca gtactctctt caacacaaat    4620
aaatgctcca aacactgggc ccaacaccac aactggatct atatctaatg atattagtgt    4680
ttggccaata attccatcag gtagcccagt tgttgacttc tatgtaagtg aagaatgaa    4740
atcattgcac atgggtggac aagcagggac ccaagccaca cactagtggg gtggtttgat    4800
ttacaggcca gagctaccgc cctcagcaac cccgccagtc tcgaagtggg agtttactgt    4860
acatgaaggt aataacatag ttggagctgg catgagctgt gttatgtttc gtgccaacga    4920
tgtagtgtct tggtcgcagg acggccagga ccttgtcggt tggtatcgtt tagacaacat    4980
aaaaacaaca caactcactg tctcttggag gcaacagaac agggttgtct atggatgggg    5040
caatgtagtc gcctggaatt cagaagagtg gcataccaat tcagagacac cacaccagcc    5100
tatattaagg ctcacatatt ggttggtcaa agtgaatgtg acagcagatc cagctgattt    5160
tgacatatta caaaaaatgc ctcttgggta tttagatccc tataatactt ctgagtcaac    5220
agcagcaatt cagaaaatca attttcagac agttcaaaaa ccatcaggtg gtaatacact    5280
tagggtgcag tactcatcaa caccgcagca aggtgatttt gttgtgatct ggcaaattgg    5340
aagacatgat tttgatatgt ctactggaaa gggtactgct gtggatactg tttcagatta    5400
tatatttcca caagcaaaag atgccgctgg tggtctttgg tatcgggcac ttacaatggt    5460
tggtcctagg actgacagga tggtcttaca tttctactat ccaactgcaa ctgatgacct    5520
tgttgaacag ataataacac aaattcaaag caggtacaag ctggctcctc taccagctga    5580
ctctgattca gatacctcta gctctgattc agagatggat tgttatgatg ctttgaaaa    5640
gcttcaggtc tatgaaaatg taagacaagc tggcttgaat catgcagtgt ccgaaaattt    5700
ggcattagct gctgtgaaga aaaaattgcg ccgaggccac gccgagtagg atcgagggta    5760
caggtaggat cgagggtaca ggtaggatcg aggg                                5794
```

<210> SEQ ID NO 6
<211> LENGTH: 655
<212> TYPE: PRT
<213> ORGANISM: Astrovirus

<400> SEQUENCE: 6

```
Ser Gln Gln Ile Lys Ser Ile Tyr Asn Asp Gln Leu Phe Asn Trp Leu
1               5                   10                  15

Leu Tyr Ile Ser Thr Leu Thr Tyr Thr Trp Thr Ala Val Ala Leu Ala
            20                  25                  30

Ile Gly Thr Tyr Tyr Met Ile Lys Ala Glu Asn Pro Ile Tyr Met Leu
        35                  40                  45

Ile Thr Leu Ile Met Ala Thr Ile Ser Lys Met Gln Leu Phe Ala Val
    50                  55                  60

Ser Ala Ile Pro Asn Met Glu Met Thr Ser Met Phe Ser Leu Trp Cys
65                  70                  75                  80

Cys Met Ala Leu Tyr Val Leu Asn Gln Ala Ala Met Ala Ala Ser
            85                  90                  95

Leu Met Ile Ala Met Leu Cys Ser Val Ile Cys Leu Phe Met Gly Asp
        100                 105                 110
```

```
Ala Glu Tyr Ile Gln Val Ile Arg Gly His Gly Val Ile Ile Thr
            115                 120                 125
Ile Val Leu Ser His Val Phe His Val Leu Gln Ile Pro Asn Trp Val
130                 135                 140
Thr Val Leu Val Ile Val Ala Leu Arg Ile Ile Arg Leu Met Ser Ala
145                 150                 155                 160
Val Ile Gly Glu Lys Ile Glu Ile Arg Asn Ile Asp Gly Lys Val Val
                165                 170                 175
Asn Val Ile Pro Thr Thr Thr Ser Trp Leu Asn Arg Val Ser Gly Phe
            180                 185                 190
Val Gln Ser Lys Phe Arg Gln Lys Val Arg Thr Gly Ile Val Ser Thr
        195                 200                 205
Ala Arg Val Ile Pro Asn Gly Val Val Val Glu Ser Lys Glu Thr
210                 215                 220
Ser Gly Thr Gly Phe Arg Val Gln Asn Tyr Ile Val Thr Ala Ala His
225                 230                 235                 240
Val Val Gly Asn Glu Thr Gln Leu Lys Val Lys Trp Gly Asp Val Val
                245                 250                 255
Val Tyr Ser Lys Val Val Tyr Ile His Pro Asn Lys Asp Val Ala Tyr
            260                 265                 270
Ile Thr Leu Pro Ala Glu Phe Gln Ala Leu Pro Thr Tyr Lys Phe Ala
        275                 280                 285
Lys Thr Val Glu Asp Gly Thr Ile Val Ile Thr Ser Leu Glu Asp Cys
    290                 295                 300
Gly Val Leu Ala Val Ala Val Ser Glu Gly Val Val Val Lys Asp Asn
305                 310                 315                 320
Met Thr Tyr Ala Ile Gln Thr Lys Asn Gly Met Ser Gly Ser Pro Val
                325                 330                 335
Thr Asn Val Asp Gly Arg Ile Ile Gly Val His Gln Ser Asn Thr Gly
            340                 345                 350
Phe Thr Gly Gly Ala Val Ile Ile Arg Pro Glu Asp Leu Pro Pro Gln
        355                 360                 365
Lys Lys Pro Gln Arg Glu Leu Glu Leu Glu Ala Lys Ile Lys Glu Leu
    370                 375                 380
Glu Glu Thr Leu Lys Ser Gln Met Asn Gln Gly Leu Asn Glu Asn Gln
385                 390                 395                 400
Ile Val Asp Leu Ile Arg Leu Ala Val Gly Arg Glu Leu Glu Ile Leu
                405                 410                 415
Arg His Glu Met Asn Leu Asn Gln Ala Lys Gly Lys Asn Lys His Arg
            420                 425                 430
Gly Lys His Gly Ala Arg Arg Arg Lys Val Arg Val Trp Thr Glu
        435                 440                 445
Glu Glu Tyr Lys Asp Leu Leu Glu Lys Gly Phe Ser Arg Gln Gln Leu
450                 455                 460
Arg Asp Met Ala Asp Val Leu Arg Glu Ala Glu Tyr Thr Asp Asp Asp
465                 470                 475                 480
Ser Glu Asp Phe Ala Glu Glu Gly Tyr Pro Gln Trp Ser Asp Pro
                485                 490                 495
Glu Asp Tyr Glu Glu Ile Glu Arg Glu Trp Phe Gly Pro Lys Lys Lys
            500                 505                 510
Ile Leu Asp Glu Val Glu Asp Gly Trp Ser Lys Thr Asp Phe Trp Glu
        515                 520                 525
Gln Cys Gln Lys Ile Trp Lys Glu Thr Glu Pro Met Pro Glu Glu Ser
    530                 535                 540
```

Val Asn Thr Leu Pro Ser His Leu His Asp Lys Tyr Gly Leu Thr Cys
545                 550                 555                 560

Tyr Val Val Thr Lys Ala Asp Met Gln Ala Leu Ala Lys Asp Leu Gln
                565                 570                 575

Glu Tyr Gln Gln Lys Val Glu Asp Lys Ile Lys Thr Asn Val Val Arg
            580                 585                 590

Gly Gln Trp Val Ser Gly Ile Asp Pro Lys Val Val Ile Thr Glu Leu
        595                 600                 605

Asp Glu Leu Trp Leu Lys Leu Asn His Leu Met Trp Ser His Gly Leu
    610                 615                 620

Val Pro Phe Ile Gln Arg Lys Lys Ile Asn Arg Arg Lys Gln Gln Lys
625                 630                 635                 640

Asn Leu Lys Gly Ala Pro Lys Ser Gly Pro Gln Asn Gln Thr Asn
                645                 650                 655

<210> SEQ ID NO 7
<211> LENGTH: 1162
<212> TYPE: PRT
<213> ORGANISM: Astrovirus

<400> SEQUENCE: 7

Ser Gln Gln Ile Lys Ser Ile Tyr Asn Asp Gln Leu Phe Asn Trp Leu
1               5                   10                  15

Leu Tyr Ile Ser Thr Leu Thr Tyr Thr Trp Thr Ala Val Ala Leu Ala
            20                  25                  30

Ile Gly Thr Tyr Tyr Met Ile Lys Ala Glu Asn Pro Ile Tyr Met Leu
        35                  40                  45

Ile Thr Leu Ile Met Ala Thr Ile Ser Lys Met Gln Leu Phe Ala Val
    50                  55                  60

Ser Ala Ile Pro Asn Met Glu Met Thr Ser Met Phe Ser Leu Trp Cys
65                  70                  75                  80

Cys Met Ala Leu Tyr Val Leu Asn Gln Ala Ala Met Ala Ala Ser
                85                  90                  95

Leu Met Ile Ala Met Leu Cys Ser Val Ile Cys Leu Phe Met Gly Asp
            100                 105                 110

Ala Glu Tyr Ile Gln Val Ile Arg Gly His Gly Val Val Ile Ile Thr
        115                 120                 125

Ile Val Leu Ser His Val Phe His Val Leu Gln Ile Pro Asn Trp Val
    130                 135                 140

Thr Val Leu Val Ile Val Ala Leu Arg Ile Ile Arg Leu Met Ser Ala
145                 150                 155                 160

Val Ile Gly Glu Lys Ile Glu Ile Arg Asn Ile Asp Gly Lys Val Val
                165                 170                 175

Asn Val Ile Pro Thr Thr Thr Ser Trp Leu Asn Arg Val Ser Gly Phe
            180                 185                 190

Val Gln Ser Lys Phe Arg Gln Lys Val Arg Thr Gly Ile Val Ser Thr
        195                 200                 205

Ala Arg Val Ile Pro Asn Gly Val Val Val Glu Ser Lys Glu Thr
    210                 215                 220

Ser Gly Thr Gly Phe Arg Val Gln Asn Tyr Ile Val Thr Ala Ala His
225                 230                 235                 240

Val Val Gly Asn Glu Thr Gln Leu Lys Val Lys Trp Gly Asp Val Val
                245                 250                 255

Val Tyr Ser Lys Val Val Tyr Ile His Pro Asn Lys Asp Val Ala Tyr
            260                 265                 270

```
Ile Thr Leu Pro Ala Glu Phe Gln Ala Leu Pro Thr Tyr Lys Phe Ala
            275                 280                 285

Lys Thr Val Glu Asp Gly Thr Ile Val Ile Thr Ser Leu Glu Asp Cys
            290                 295                 300

Gly Val Leu Ala Val Ala Val Ser Glu Gly Val Val Lys Asp Asn
305                 310                 315                 320

Met Thr Tyr Ala Ile Gln Thr Lys Asn Gly Met Ser Gly Ser Pro Val
            325                 330                 335

Thr Asn Val Asp Gly Arg Ile Ile Gly Val His Gln Ser Asn Thr Gly
            340                 345                 350

Phe Thr Gly Gly Ala Val Ile Ile Arg Pro Glu Asp Leu Pro Pro Gln
            355                 360                 365

Lys Lys Pro Gln Arg Glu Leu Glu Leu Glu Ala Lys Ile Lys Glu Leu
            370                 375                 380

Glu Glu Thr Leu Lys Ser Gln Met Asn Gln Gly Leu Asn Glu Asn Gln
385                 390                 395                 400

Ile Val Asp Leu Ile Arg Leu Ala Val Gly Arg Glu Leu Glu Ile Leu
            405                 410                 415

Arg His Glu Met Asn Leu Asn Gln Ala Lys Gly Lys Asn Lys His Arg
            420                 425                 430

Gly Lys His Gly Ala Arg Arg Arg Lys Val Arg Val Trp Thr Glu
            435                 440                 445

Glu Glu Tyr Lys Asp Leu Leu Glu Lys Gly Phe Ser Arg Gln Gln Leu
            450                 455                 460

Arg Asp Met Ala Asp Val Leu Arg Glu Ala Glu Tyr Thr Asp Asp Asp
465                 470                 475                 480

Ser Glu Asp Phe Ala Glu Glu Gly Tyr Pro Gln Trp Ser Asp Pro
            485                 490                 495

Glu Asp Tyr Glu Glu Ile Glu Arg Glu Trp Phe Gly Pro Lys Lys Lys
            500                 505                 510

Ile Leu Asp Glu Val Glu Asp Gly Trp Ser Lys Thr Asp Phe Trp Glu
            515                 520                 525

Gln Cys Gln Lys Ile Trp Lys Glu Thr Glu Pro Met Pro Glu Glu Ser
            530                 535                 540

Val Asn Thr Leu Pro Ser His Leu His Asp Lys Tyr Gly Leu Thr Cys
545                 550                 555                 560

Tyr Val Val Thr Lys Ala Asp Met Gln Ala Leu Ala Lys Asp Leu Gln
            565                 570                 575

Glu Tyr Gln Gln Lys Val Glu Asp Lys Ile Lys Thr Asn Val Val Arg
            580                 585                 590

Gly Gln Trp Val Ser Gly Ile Asp Pro Lys Val Val Ile Thr Glu Leu
            595                 600                 605

Asp Glu Leu Trp Leu Lys Leu Asn His Leu Met Trp Ser His Gly Leu
            610                 615                 620

Val Pro Phe Ile Gln Arg Lys Lys Ile Asn Arg Arg Lys Gln Gln Lys
625                 630                 635                 640

Leu Glu Gly Gly Pro Glu Val Gly Ala Pro Lys Pro Asp Gln Leu Arg
            645                 650                 655

Leu Asp Ser Trp Lys Gln Met Leu Glu Pro Gly Glu Tyr Phe Leu Thr
            660                 665                 670

Pro Val Asn Cys Pro Leu Ile Gly Val Leu Pro Ile Asp Arg Pro Ile
            675                 680                 685

Ser Asp Tyr Asp Glu Pro Val Asp Asp Leu Leu Asn Leu Leu Pro Lys
```

690             695             700

Cys Asp Glu Asp Pro Pro Tyr Ala Pro Ser Thr Trp Gly Pro Glu Ala
705             710                 715                 720

Tyr Arg Lys Ser Phe Gln Lys Phe Phe Tyr Lys Glu Pro Val Lys Asn
            725                 730                 735

Ile Lys Glu Lys Tyr Lys Arg Glu Trp Lys Phe Ala Met Ser Ala Leu
                740                 745                 750

Arg Arg Glu Phe Asp Phe Leu Asn Asp Ser Val Met Ile Asp Ile Thr
            755                 760                 765

Ala Thr Ser Lys Asn Ala Asp Ser Thr Pro Ala Tyr Pro Lys Thr Leu
        770                 775                 780

Trp Trp Lys Thr Glu Thr Asp Tyr Leu Lys Asp Arg Gly Tyr Gln Asp
785             790                 795                 800

Tyr Ile Thr Glu Leu Asp Arg Ile Met Asp Gly Asp Arg Pro Asp Val
                805                 810                 815

Leu Trp Tyr Leu Phe Leu Lys Lys Glu Ile Leu Lys Ile Ser Lys Ile
            820                 825                 830

Glu Asp Glu Asp Ile Arg Gln Ile Val Cys Ser Asp Pro Ile Phe Ala
                835                 840                 845

Arg Ile Gly Cys Val Phe Glu Glu Asn Gln Asn Gln Leu Met Lys Gly
850                 855                 860

Arg Thr Leu Thr Arg Met Gly Gln Cys Gly Trp Ser Pro Phe Met Gly
865                 870                 875                 880

Gly Phe His Arg Arg Val Lys Arg Leu Val Asp Lys Gly Asn Asn His
                885                 890                 895

Phe Ile Glu Phe Asp Trp Thr Arg Tyr Asp Gly Thr Ile Pro Thr Glu
                900                 905                 910

Val Phe Ser Ala Ile Lys Asp Phe Arg Phe Ser Cys Leu Arg Lys Glu
            915                 920                 925

Phe Arg Thr Glu Lys Asn Lys Ser Val Tyr Asp Trp Tyr Cys Lys Asn
            930                 935                 940

Ile Phe Lys Arg Tyr Val Met Leu Pro Ser Gly Glu Val Thr Val Gln
945                 950                 955                 960

Glu Arg Gly Asn Pro Ser Gly Gln Ile Ser Thr Thr Met Asp Asn Asn
                965                 970                 975

Leu Cys Asn Val Phe Phe Gln Ala Phe Glu Phe Ala His Leu Asn Pro
            980                 985                 990

Asp Lys Thr Ile Asp Glu Leu Arg Glu Gly Trp Glu Lys Val Asp Ser
            995                 1000                1005

Leu Ile Tyr Gly Asp Asp Arg Leu Ser Thr Val Pro Tyr Val Cys
    1010                1015                1020

Ser Asn Tyr Val Glu Lys Val Ile Asp Met Tyr Glu Asn Ile Phe
    1025                1030                1035

Gly Met Trp Val Lys Pro Asn Lys Val Lys Leu Ser Asp Ser Val
    1040                1045                1050

Ile Gly Leu Thr Phe Cys Gly Phe Thr Ile Thr Met Ser Asp Asn
    1055                1060                1065

Val Tyr Val Pro Val Pro Thr Asp Thr Asp Lys Leu Leu Ala Gly
    1070                1075                1080

Leu Val Thr Pro Val Lys Lys Leu Pro Asp Ile Leu Ser Leu Tyr
    1085                1090                1095

Gly Lys Leu Leu Cys Tyr Arg Ile Leu Gly His Asn Leu Pro Asp
    1100                1105                1110

-continued

```
Asp His Lys Phe Lys Asn Tyr Ile Leu Val Ala Leu Glu Val Leu
    1115                1120                1125

Ala Arg His Ile Arg Asn Gly Gly Glu Glu Pro Tyr His Ile
    1130                1135                1140

Thr Asp Glu Met Leu Asp Arg Leu Trp Arg Gly Pro Lys Leu
    1145                1150                1155

Gly Tyr Gly Trp
    1160

<210> SEQ ID NO 8
<211> LENGTH: 755
<212> TYPE: PRT
<213> ORGANISM: Astrovirus

<400> SEQUENCE: 8

Met Ala Gly Lys Gln Pro Gln Gln Ala Met Pro Lys Ala Thr Val Lys
1               5                   10                  15

Gln Leu Ala Lys Glu Val Val Lys Gln Glu Arg Gln Val Lys Gln Asn
            20                  25                  30

Gln Pro Lys Lys Tyr Phe Pro Val Lys Asn Lys Lys Tyr Ile Lys
        35                  40                  45

Arg Glu Val Arg Lys Asp Leu Lys Lys Gln Gly Phe Glu Gly Pro Lys
50                  55                  60

Pro Arg Phe Ser Val Ser Val Ser Ala Thr Ile Gly Lys Val Gly Pro
65                  70                  75                  80

Asn Lys Ala Gln Gly Pro Glu Leu Gln Ile Ser Thr Phe Met His Pro
                85                  90                  95

Ser Leu Met Lys Glu Pro Asn Asp Gly Thr Asn Phe Gly Pro Leu Gln
            100                 105                 110

Ser Ala Ala Gln Trp Gly Leu Trp Arg Leu Lys Asn Leu Ser Val
        115                 120                 125

Thr Phe Thr Pro Leu Val Gly Pro Ser Ala Val Thr Gly Ser Val Phe
130                 135                 140

Arg Ile Ser Leu Asn Met Ala Gln Ser Pro Gly Ala Thr Ser Trp Gly
145                 150                 155                 160

Gly Leu Gly Ala Arg Lys His Arg Asp Val Ala Val Gly Lys Gln Phe
                165                 170                 175

Thr Trp Lys Leu Gln Arg Gly Asp Leu Thr Gly Pro Arg Glu Thr Trp
            180                 185                 190

Trp Leu Thr Asp Thr Asn Glu Glu Gly Ala Gln Ser Cys Gly Pro Leu
        195                 200                 205

Leu Glu Ile His Gly Leu Gly Ala Thr Thr Ser Thr Tyr Lys Asp Ala
210                 215                 220

Ala Trp Asn Gly Asp Leu Phe Ile Val Glu Val Lys Gly Arg Trp Glu
225                 230                 235                 240

Phe Ala Asn Tyr Asn Ser Lys Pro Ala Leu Gly Met Leu Glu Arg Ile
                245                 250                 255

Thr Glu Ser Thr Ser Ala Ser Ile Glu Val Thr Asp Gly Asn Met Ile
            260                 265                 270

Met Thr Val Pro Arg Ser Ser Gln Leu Ala Arg His Met Gly Glu Arg
        275                 280                 285

Tyr Glu Lys Ser Gly Asn Ala Ser Thr Val Gly Glu Thr Ile Trp Gln
290                 295                 300

Ile Val Asp Glu Gly Ala Gly Leu Val Ala Asn Ala Ala Pro Pro
305                 310                 315                 320
```

-continued

Phe Thr Trp Leu Ile Lys Gly Trp Trp Phe Val Lys Lys Leu Leu
                325                 330                 335

Gly Arg Ser Ala Asn Thr Asp Ala Gln Tyr Leu Val Tyr Ala Ser Leu
                340                 345                 350

Ala Asp Ala Gln Asn Asn Arg Pro Val Glu Ala Gln Thr Phe Pro Lys
                355                 360                 365

Thr Thr His Thr Thr Val Leu Ser Ser Thr Gln Ile Asn Ala Pro Asn
            370                 375                 380

Thr Gly Pro Asn Thr Thr Thr Gly Ser Ile Ser Asn Asp Ile Ser Val
385                 390                 395                 400

Trp Pro Ile Ile Pro Ser Gly Ser Pro Val Val Asp Phe Tyr Val Ser
                405                 410                 415

Gly Arg Met Lys Ser Leu His Met Gly Gly Gln Ala Gly Thr Gln Ala
                420                 425                 430

Thr Thr Leu Val Gly Gly Leu Ile Tyr Arg Pro Glu Leu Pro Pro Ser
            435                 440                 445

Ala Thr Pro Pro Val Ser Lys Trp Glu Phe Thr Val His Glu Gly Asn
        450                 455                 460

Asn Ile Val Gly Ala Gly Met Ser Cys Val Met Phe Arg Ala Asn Asp
465                 470                 475                 480

Val Val Ser Trp Ser Gln Asp Gly Gln Asp Leu Val Gly Trp Tyr Arg
                485                 490                 495

Leu Asp Asn Ile Lys Thr Thr Gln Leu Thr Val Ser Trp Arg Gln Gln
                500                 505                 510

Asn Arg Val Val Tyr Gly Trp Gly Asn Val Val Ala Trp Asn Ser Glu
                515                 520                 525

Glu Trp His Thr Asn Ser Glu Thr Pro His Gln Pro Ile Leu Arg Leu
        530                 535                 540

Thr Tyr Trp Leu Val Lys Val Asn Val Thr Ala Asp Pro Ala Asp Phe
545                 550                 555                 560

Asp Ile Leu Gln Lys Met Pro Leu Gly Tyr Leu Asp Pro Tyr Asn Thr
                565                 570                 575

Ser Glu Ser Thr Ala Ala Ile Gln Lys Ile Asn Phe Gln Thr Val Gln
            580                 585                 590

Lys Pro Ser Gly Gly Asn Thr Leu Arg Val Gln Tyr Ser Ser Thr Pro
        595                 600                 605

Gln Gln Gly Asp Phe Val Val Ile Trp Gln Ile Gly Arg His Asp Phe
    610                 615                 620

Asp Met Ser Thr Gly Lys Gly Thr Ala Val Asp Thr Val Ser Asp Tyr
625                 630                 635                 640

Ile Phe Pro Gln Ala Lys Asp Ala Ala Gly Gly Leu Trp Tyr Arg Ala
                645                 650                 655

Leu Thr Met Val Gly Pro Arg Thr Asp Arg Met Val Leu His Phe Tyr
                660                 665                 670

Tyr Pro Thr Ala Thr Asp Asp Leu Val Glu Gln Ile Ile Thr Gln Ile
            675                 680                 685

Gln Ser Arg Tyr Lys Leu Ala Pro Leu Pro Ala Asp Ser Asp Ser Asp
        690                 695                 700

Thr Ser Ser Ser Asp Ser Glu Met Asp Cys Tyr Asp Gly Phe Glu Lys
705                 710                 715                 720

Leu Gln Val Tyr Glu Asn Val Arg Gln Ala Gly Leu Asn His Ala Val
                725                 730                 735

Ser Glu Asn Leu Ala Leu Ala Ala Val Lys Lys Lys Leu Arg Arg Gly
            740                 745                 750

His Ala Glu
    755

<210> SEQ ID NO 9
<211> LENGTH: 23
<212> TYPE: DNA
<213> ORGANISM: Artificial Sequence
<220> FEATURE:
<223> OTHER INFORMATION: Primer panAV-F11

<400> SEQUENCE: 9
garttygatt ggrckcgkta yga                                              23

<210> SEQ ID NO 10
<211> LENGTH: 23
<212> TYPE: DNA
<213> ORGANISM: Artificial Sequence
<220> FEATURE:
<223> OTHER INFORMATION: Primer panAV-F12

<400> SEQUENCE: 10
garttygatt ggrckaggta yga                                              23

<210> SEQ ID NO 11
<211> LENGTH: 19
<212> TYPE: DNA
<213> ORGANISM: Artificial Sequence
<220> FEATURE:
<223> OTHER INFORMATION: Primer panAV-R1
<220> FEATURE:
<221> NAME/KEY: misc_feature
<222> LOCATION: (14)..(14)
<223> OTHER INFORMATION: n is deoxyinosine

<400> SEQUENCE: 11
gyttkaccca catnccraa                                                   19

<210> SEQ ID NO 12
<211> LENGTH: 20
<212> TYPE: DNA
<213> ORGANISM: Artificial Sequence
<220> FEATURE:
<223> OTHER INFORMATION: Primer panAV-F21
<220> FEATURE:
<221> NAME/KEY: misc_feature
<222> LOCATION: (18)..(18)
<223> OTHER INFORMATION: n is deoxyinosine

<400> SEQUENCE: 12
cgktaygatg gkackatncc                                                  20

<210> SEQ ID NO 13
<211> LENGTH: 20
<212> TYPE: DNA
<213> ORGANISM: Artificial Sequence
<220> FEATURE:
<223> OTHER INFORMATION: Primer panAV-F22
<220> FEATURE:
<221> NAME/KEY: misc_feature
<222> LOCATION: (18)..(18)
<223> OTHER INFORMATION: n is deoxyinosine

<400> SEQUENCE: 13
aggtaygatg gkackatncc                                                  20

<210> SEQ ID NO 14
<211> LENGTH: 59
<212> TYPE: DNA

```
<213> ORGANISM: Artificial Sequence
<220> FEATURE:
<223> OTHER INFORMATION: Primer DT-01
<220> FEATURE:
<221> NAME/KEY: misc_feature
<222> LOCATION: (59)..(59)
<223> OTHER INFORMATION: n is a, c, g, or t

<400> SEQUENCE: 14
attctagagg ccgaggcggc cgacatgttt tttttttttt tttttttttt tttttttvn      59

<210> SEQ ID NO 15
<211> LENGTH: 21
<212> TYPE: DNA
<213> ORGANISM: Artificial Sequence
<220> FEATURE:
<223> OTHER INFORMATION: Primer 295-3end-F1

<400> SEQUENCE: 15
gtcaatacca tctactgggc a                                                21

<210> SEQ ID NO 16
<211> LENGTH: 21
<212> TYPE: DNA
<213> ORGANISM: Artificial Sequence
<220> FEATURE:
<223> OTHER INFORMATION: Primer DT-02

<400> SEQUENCE: 16
attctagagg ccgaggcggc c                                                21

<210> SEQ ID NO 17
<211> LENGTH: 24
<212> TYPE: DNA
<213> ORGANISM: Artificial Sequence
<220> FEATURE:
<223> OTHER INFORMATION: Primer 295-5end-R-1

<400> SEQUENCE: 17
ggtttttact ggtgtagtta ctgg                                             24

<210> SEQ ID NO 18
<211> LENGTH: 23
<212> TYPE: DNA
<213> ORGANISM: Artificial Sequence
<220> FEATURE:
<223> OTHER INFORMATION: Primer 295-5end-R-2

<400> SEQUENCE: 18
actggtgtag ttactggctg cac                                              23

<210> SEQ ID NO 19
<211> LENGTH: 36
<212> TYPE: DNA
<213> ORGANISM: Artificial Sequence
<220> FEATURE:
<223> OTHER INFORMATION: Primer PPC01
<220> FEATURE:
<221> NAME/KEY: misc_feature
<222> LOCATION: (24)..(25)
<223> OTHER INFORMATION: n is deoxyinosine
<220> FEATURE:
<221> NAME/KEY: misc_feature
<222> LOCATION: (29)..(29)
<223> OTHER INFORMATION: n is deoxyinosine
<220> FEATURE:
<221> NAME/KEY: misc_feature
<222> LOCATION: (34)..(34)
<220> FEATURE:
<221> NAME/KEY: misc_feature
```

```
<222> LOCATION: (34)..(34)
<223> OTHER INFORMATION: n is deoxyinosine

<400> SEQUENCE: 19
ggccacgcgt cgactagtac gggnngggng gggngg                       36

<210> SEQ ID NO 20
<211> LENGTH: 33
<212> TYPE: RNA
<213> ORGANISM: Artificial Sequence
<220> FEATURE:
<223> OTHER INFORMATION: Synthetic construct: HMOAstV consensus

<400> SEQUENCE: 20
cuuuggaggg gmggwccaaa gydwrgwbau ggc                          33

<210> SEQ ID NO 21
<211> LENGTH: 4
<212> TYPE: PRT
<213> ORGANISM: Artificial Sequence
<220> FEATURE:
<223> OTHER INFORMATION: Synthetic construct

<400> SEQUENCE: 21

Tyr Gly Asp Asp
1
```

ASTROVIRUS SPECIES

RELATED APPLICATIONS

This application is a utility application and claims priority under 35 U.S.C. §119(e) to U.S. Provisional application Ser. No. 61/235,126 filed Aug. 19, 2009, the entire content of which is incorporated herein by reference.

GRANT INFORMATION

This invention was made in part with government support under NIH Grant No. R01 HL083254 awarded by the National Institutes of Health. The United States government has certain rights in this invention.

FIELD OF THE INVENTION

The present invention relates generally to the discovery of new astrovirus species and more specifically, to methods of using the virus including methods of detecting the virus and diagnosing viral infection, methods of treating or preventing virus infection, and methods for identifying anti-viral compounds.

BACKGROUND OF THE INVENTION

The Astroviridae are non-enveloped, small (28 to 30 nm in diameter), single-stranded positive sense RNA viruses whose genomes range in size from 6.4 kb to 7.3 kb. The genome includes three open reading frames (ORFs) designated ORF1a, ORF1b, and ORF2. ORF1a encodes the non-structural polyprotein 1a while the longer ORF1b encodes polyprotein 1ab including the RNA dependent RNA polymerase (RdRp) expressed through a ribosomal frameshift at the ORF1a/1b junction mediated by a slippery polyA sequence. ORF2 encodes the viral structural polyprotein (Mendez & Arias (2007) Astroviridae. In *Fields Virology*, pp. 981-1000. Edited by D. M. Knipe and P. M. Howley. Philadelphia: Lippincott Williams & Wilkins; Monroe et al. (2005) Astroviridae. In *Virus Taxonomy. Eighth Report of the International Committee on Taxonomy of Viruses*, pp. 859-64. Edited by C. M. Fauquet, M. A. Mayo, J. Maniloff, U. Desselberger and L. A. Ball. Amsterdam Elsevier Academic Press).

The family Astroviridae consists so far of two genera, *Avastrovirus* and *Mamastrovirus*, that infects avian and mammalian hosts respectively. Astroviruses, transmitted through the fecal-oral route cause gastroenteritis in mammalian and avian species including humans, calves, piglets, sheep, minks, dogs, cats, mice, chickens, and turkeys (Jonassen et al. (2001) *J. Gen. Virol.* 82:1061-67; Jonassen et al. (2003) *Virus Res.* 91:195-201). All eight known human astroviruses serotypes belonging to the first identified human astrovirus species (HAstV) have been associated with gastroenteritis (Clark & McKendrick (2004) *Curr. Opin. Infect. Dis.* 17:461-69; Fodha et al. (2006) *J. Med. Virol.* 78:1198-1203; Gabbay et al. (2007) *Mem. Inst. Oswaldo Cruz* 102:531-34; Jin et al. (2009) *J. Clin. Virol.* 44:238-41; Tayeb et al. (2008) *J. Med. Virol.* 80:1919-29). Clinical symptoms of HAstV infection in humans usually last between two and four days and consist of watery diarrhea and, less commonly, vomiting, headache, fever, abdominal pains, and anorexia (Mendez & Arias (2007) Astroviridae. In *Fields Virology*, pp. 981-1000. Edited by D. M. Knipe and P. M. Howley. Philadelphia: Lippincott Williams & Wilkins; Monroe et al. (2005) Astroviridae. In *Virus Taxonomy. Eighth Report of the International Committee on Taxonomy of Viruses*, pp. 859-64. Edited by C. M. Fauquet, M. A. Mayo, J. Maniloff, U. Desselberger and L. A. Ball. Amsterdam Elsevier Academic Press). HAstV can also cause significant disease in the elderly and in immunocompromised patients (Liste et al. (2000) *J. Clin. Microbial.* 38:2873-77). Recently a second species of astrovirus was found in a child with diarrhea and named AstV-MLB (Finkbeiner et al. (2008) *Virol. J.* 5:117).

Group reactive or pan-PCR approaches have been successfully used to identify new viruses in humans (Oberste et al. (2005) *J. Gen. Viral.* 86:445-51; Oberste et al. (2004) *J. Gen. Virol.* 85:3205-3212), animals (Atkins et al. (2009) *Vet. Microbial.* 136:160-65; Nollens et al. (2008) *Vet. Microbial.* 128:231-42; Smith et al. (2008) *Vet. Microbial.* 129:236-45; Wellehan et al. (2008) *Vet. Microbial.* 127:249-57; Wellehan et al. (2009) *Vet. Microbial.* 133:34-42; Zhu et al. (2009) *J. Gen. Virol.* 90:883-87) and environmental samples (Culley et al. (2003) *Nature* 424:1054-57; Culley et al. (2007) *Virol. J.* 4:69; Culley & Steward (2007) *Appl. Environ. Microbial.* 73:5937-44).

Despite the known pathogenicity of astroviruses and the urgent need for methods to prevent, diagnose and treat astrovirus infections, other divergent human astroviruses have not yet been identified. Therefore, a need exists to detect divergent human astroviruses and to provide a method to diagnose, prevent and treat astroviruses infection. Moreover, there exists a need to provide methods to identify astroviruses antiviral compounds.

SUMMARY OF THE INVENTION

The present invention relates to a new astrovirus species. Accordingly, the present invention provides the genomic sequences of 2 variants of astrovirus, and the sequences of the viral proteins encoded thereby. The variants have been termed Human Mink and Ovine-like Astroviurus (HMOAstV),-A and HMOAstV-B. Also provided are methods of detecting the new astrovirus variants and diagnosing astrovirus infection in biological samples, methods of treating or preventing astrovirus infection, and methods for identifying antiviral compounds.

Accordingly, in one embodiment of the present invention, there are provided isolated nucleic acid molecules obtained from new astrovirus variants. In certain embodiments, the isolated nucleic acid molecule comprises a nucleotide sequence having at least 75% identity to SEQ ID NO:1, SEQ ID NO:5, or a complement thereof, which may be the full-length complement thereof. In some embodiments, the isolated nucleic acid molecule comprises a nucleotide sequence having at least 75% identity to SEQ ID NO:1, SEQ ID NO:5, or a complement thereof, which may be the full-length complement thereof, wherein the nucleotide sequence is at least 12, 20, 25, 30, 40, 50, 75, 100, or 200 nucleotides in length. In some embodiments, the isolated nucleic acid molecule comprises a nucleotide sequence selected from the group consisting of SEQ ID NO:1, SEQ ID NO:5, and a complement thereof, which may be the full-length complement thereof.

In another embodiment, the isolated nucleic acid molecule comprises a nucleotide sequence that hybridizes under highly stringent conditions to at least 12, 25, 50, 100, or 150 contiguous nucleotides of a nucleotide sequence of SEQ ID NO:1, SEQ ID NO:5, or a complement thereof, which may be the full-length complement thereof, wherein the hybridization reaction is incubated at 42° C. in a solution comprising 50% formamide, 5×SSC, and 1% SDS and washed at 65° C. in a solution comprising 0.2×SSC and 0.1% SDS. In one aspect, the nucleotide sequence hybridizes under highly stringent conditions over the full length of SEQ ID NO:1, SEQ ID NO:5, or a complement thereof, which may be the full-length complement thereof, wherein the hybridization reaction is incubated at 42° C. in a solution comprising 50% formamide, 5×SSC, and 1% SDS and washed at 65° C. in a solution comprising 0.2×SSC and 0.1% SDS.

In another embodiment, the isolated nucleic acid molecule comprises a nucleotide sequence that hybridizes under highly stringent conditions to at least 12, 25, 50, 100, or 150 contiguous nucleotides of a nucleotide sequence encoding a protein selected from the group consisting of SEQ ID NO:2, SEQ ID NO:3, SEQ ID NO:4, SEQ ID NO:6, SEQ ID NO:7, SEQ ID NO:8, or a complement thereof, which may be the full-length complement thereof, wherein the hybridization reaction is incubated at 42° C. in a solution comprising 50% formamide, 5×SSC, and 1% SDS and washed at 65° C. in a solution comprising 0.2×SSC and 0.1% SDS. In one aspect, the nucleotide sequence hybridizes under highly stringent conditions over the full length of a nucleotide sequence encoding a protein selected from the group consisting of SEQ ID NO:2, SEQ ID NO:3, SEQ ID NO:4, SEQ ID NO:6, SEQ ID NO:7, SEQ ID NO:8, or a complement thereof, which may be the full-length complement thereof, wherein the hybridization reaction is incubated at 42° C. in a solution comprising 50% formamide, 5×SSC, and 1% SDS and washed at 65° C. in a solution comprising 0.2×SSC and 0.1% SDS.

In certain embodiments, the isolated nucleic acid molecule comprises a nucleotide sequence which is at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:1, SEQ ID NO:5, or a complement thereof, which may be the full-length complement thereof. In one aspect, the nucleotide sequence is at least 80% identical to SEQ ID NO:1, SEQ ID NO:5, or a complement thereof, which may be the full-length complement thereof. In another aspect, the nucleotide sequence is at least 90% identical to SEQ ID NO:1, SEQ ID NO:5, or a complement thereof, which may be the full-length complement thereof. In another aspect, the nucleotide sequence is at least 95% identical to SEQ ID NO:1, SEQ ID NO:5, or a complement thereof, which may be the full-length complement thereof.

In certain embodiments, the isolated nucleic acid molecule comprises a nucleotide sequence comprising an open reading frame. In one aspect, the nucleotide sequence comprises an open reading frame encoding a protein selected from the group consisting of SEQ ID NO:2, SEQ ID NO:3, SEQ ID NO:4, SEQ ID NO:6, SEQ ID NO:7, SEQ ID NO:8.

In another embodiment of the present invention, there are provided substantially purified proteins encoded by any nucleotide sequences described above. In one aspect, the substantially purified protein comprises an amino acid sequence at least 80% identical to an amino acid sequence selected from the group consisting of SEQ ID NO:2, SEQ ID NO:3, SEQ ID NO:4, SEQ ID NO:6, SEQ ID NO:7, and SEQ ID NO:8. In another aspect, the substantially purified protein comprises an amino acid sequence at least 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from the group consisting of SEQ ID NO:2, SEQ ID NO:3, SEQ ID NO:4, SEQ ID NO:6, SEQ ID NO:7, and SEQ ID NO:8. In another aspect, the substantially purified protein comprises an amino acid sequence selected from the group consisting of SEQ ID NO:2, SEQ ID NO:3, SEQ ID NO:4, SEQ ID NO:6, SEQ ID NO:7, and SEQ ID NO:8. In another aspect, the substantially purified protein comprises an amino acid sequence selected from the group consisting of SEQ ID NO:2, SEQ ID NO:3, SEQ ID NO:4, SEQ ID NO:6, SEQ ID NO:7, and SEQ ID NO:8.

In another embodiment of the present invention, there are provided a composition comprising any substantially purified proteins described above. In another embodiment, there are provided a composition comprising any substantially purified proteins encoded by any nucleotide sequences described above. In another embodiment, there are provided a composition comprising any nucleotide sequences described above.

In another embodiment of the present invention, there are provided an isolated antibody which specifically binds to any substantially purified proteins described above. In another embodiment, there are provided an isolated antibody which specifically binds to any proteins encoded by any nucleotide sequences described above. In another embodiment of the present invention, there are provided a purified serum composition comprising a polyclonal antibody that specifically binds to any substantially purified proteins described above. In another embodiment, there are provided a purified serum composition comprising a polyclonal antibody that specifically binds to any proteins encoded by any nucleotide sequences described above.

In another embodiment of the present invention, there are provided an isolated astrovirus comprising any nucleotide sequences described above. In another embodiment of the present invention, there are provided an expression vector comprising any nucleotide sequences described above. In one aspect, there are provided a host cell comprising the expression vector comprising any nucleotide sequences described above.

In still another embodiment of the invention, there is provided a method of detecting an astrovirus nucleic acid molecule by hybridization to a probe. In some embodiments, the method of detecting an astrovirus nucleic acid comprises: (a) contacting a sample suspected of containing an astrovirus nucleic acid with a nucleotide sequence that hybridizes under highly stringent conditions to a nucleotide sequence of SEQ ID NO:1, SEQ ID NO:5, or a complement thereof, which may be the full-length complement thereof; and (b) detecting the presence or absence of hybridization. In some embodiments, the method of detecting an astrovirus nucleic acid comprises: (a) contacting a sample suspected of containing an astrovirus nucleic acid with a nucleotide sequence that hybridizes under highly stringent conditions to a nucleotide sequence encoding an amino acid sequence selected from the group consisting of SEQ ID NO:2, SEQ ID NO:3, SEQ ID NO:4, SEQ ID NO:6, SEQ ID NO:7, and SEQ ID NO:8, or a complement thereof, which may be the full-length complement thereof; and (b) detecting the presence or absence of hybridization. In one aspect, the hybridization conditions include hybridizing at 42° C. in a solution comprising 50% formamide, 5×SSC, and 1% SDS and washing at 65° C. in a solution comprising 0.2×SSC and 0.1% SDS.

In yet another embodiment of the invention, there is provided a method of detecting an astrovirus nucleic acid molecule by detection of a nucleic acid amplification product. In some embodiments, the method of detecting an astrovirus nucleic acid comprises: (a) amplifying the nucleic acid of a sample suspected of containing astrovirus nucleic acid with at least one primer that hybridizes to a nucleotide sequence of SEQ ID NO:1, SEQ ID NO:5, or a complement thereof, which may be the full-length complement thereof, to produce an amplification product; and (b) detecting the presence of an amplification product, thereby detecting the presence of the astrovirus nucleic acid. In some embodiments, the method of detecting an astrovirus nucleic acid comprises: (a) amplifying the nucleic acid of a sample suspected of containing astrovirus nucleic acid with at least one primer that hybridizes to a nucleotide sequence encoding an amino acid sequence selected from the group consisting of SEQ ID NO:2, SEQ ID NO:3, SEQ ID NO:4, SEQ ID NO:6, SEQ ID NO:7, and SEQ ID NO:8, or a complement thereof, which may be the full-length complement thereof, to produce an amplification product; and (b) detecting the presence of an amplification product, thereby detecting the presence of the astrovirus nucleic acid. In one aspect, the amplifying includes a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles.

In another embodiment of the present invention, there is provided a method of detecting an astrovirus infection in a subject by detecting a protein of the invention in a sample from the subject. In one aspect, the method of detecting an astrovirus infection in a sample comprises: (a) contacting a sample suspected of containing an astrovirus protein with an antibody that specifically binds to a polypeptide encoded by SEQ ID NO:1 or SEQ ID NO:5 to form a protein/antibody complex; and (b) detecting the presence of the protein/antibody complex, thereby detecting the presence of the astrovirus protein. In another aspect, the method of detecting an astrovirus infection in a sample comprises: (a) contacting a sample suspected of containing an astrovirus protein with an antibody that specifically binds to an amino acid sequence selected from the group consisting of SEQ ID NO:2, SEQ ID NO:3, SEQ ID NO:4, SEQ ID NO:6, SEQ ID NO:7, and SEQ ID NO:8 to form a protein/antibody complex; and (b) detecting the presence of the protein/antibody complex, thereby detecting the presence of the astrovirus protein.

The invention also contemplates a kit for detecting an astrovirus nucleic acid, the kit containing at least one nucleic acid molecule that hybridizes under highly stringent conditions to any nucleotide sequences described above. In one aspect, the kit comprises a nucleic acid molecule having a nucleotide sequence of SEQ ID NO:1, SEQ ID NO:5, or a complement thereof, which may be the full-length complement thereof. In another aspect, the kit comprises a nucleic acid molecule having a nucleotide sequence encoding an amino acid sequence selected from the group consisting of SEQ ID NO:2, SEQ ID NO:3, SEQ ID NO:4, SEQ ID NO:6, SEQ ID NO:7, SEQ ID NO:8, or a complement thereof, which may be the full-length complement thereof. In one aspect, the hybridization conditions include hybridizing at 42° C. in a solution comprising 50% formamide, 5×SSC, and 1% SDS and washing at 65° C. in a solution comprising 0.2×SSC and 0.1% SDS.

The invention also contemplates a kit for detecting an astrovirus nucleic acid, the kit containing at least one oligonucleotide primer. In one aspect, the kit comprises at least one oligonucleotide primer that hybridizes to a nucleotide sequence of SEQ ID NO:1, SEQ ID NO:5, or a complement thereof, which may be the full-length complement thereof, under highly stringent PCR conditions. In another aspect, the kit comprises at least one oligonucleotide primer that hybridizes to a nucleotide sequence encoding an amino acid sequence selected from the group consisting of SEQ ID NO:2, SEQ ID NO:3, SEQ ID NO:4, SEQ ID NO:6, SEQ ID NO:7, SEQ ID NO:8, or a complement thereof, which may be the full-length complement thereof, under highly stringent PCR conditions. In one aspect, the PCR conditions comprise a denaturation phase of 90° C.-95° C. for 30 sec-2 min., an annealing phase of 50° C. to about 65° C. lasting 30 sec.-2 min., and an extension phase of about 72° C. for 1-2 min., and an extension phase of about 72° C. for 1-2 min for 20-40 cycles.

The invention also contemplates a kit for detecting an astrovirus, the kit containing an antibody. In one aspect, the kit comprises an antibody that detects a polypeptide encoded by SEQ ID NO:1 or SEQ ID NO:5. In another aspect, the kit comprises an antibody that detects an amino acid sequence selected from the group consisting of SEQ ID NO:2, SEQ ID NO:3, SEQ ID NO:4, SEQ ID NO:6, SEQ ID NO:7, SEQ ID NO:8. In one aspect, the kit contains a monoclonal antibody. In another aspect, the kit contains a polyclonal antibody.

In another embodiment of the present invention, there is provided a method of assaying for an anti-astrovirus compound. In one aspect, the method comprises: (a) contacting a sample containing an astrovirus with a test compound, the astrovirus comprising a genome that hybridizes under highly stringent conditions to a nucleotide sequence of SEQ ID NO:1, SEQ ID NO:5, or a complement thereof, which may be the full-length complement thereof; and (b) determining whether the test compound inhibits astrovirus replication, wherein inhibition of astrovirus replication indicates that the test compound is an anti-astrovirus compound. In another aspect, the method comprises: (a) contacting a sample containing an astrovirus with a test compound, the astrovirus comprising a genome that hybridizes under highly stringent conditions to a nucleotide sequence encoding an amino acid sequence selected from the group consisting of SEQ ID NO:2, SEQ ID NO:3, SEQ ID NO:4, SEQ ID NO:6, SEQ ID NO:7, SEQ ID NO:8, or a complement thereof, which may be the full-length complement thereof; and (b) determining whether the test compound inhibits astrovirus replication, wherein inhibition of astrovirus replication indicates that the test compound is an anti-astrovirus compound. In one aspect, the hybridization reaction is incubated at 42° C. in a solution comprising 50% formamide, 5×SSC, and 1% SDS and washed at 65° C. in a solution comprising 0.2×SSC and 0.1% SDS.

In still another embodiment of the present invention, there is provided a method of at least partially treating or preventing an astrovirus infection in a subject. In one aspect, the method comprises administering to the subject an antigen encoded by an astrovirus, the astrovirus comprising a genome that hybridizes under highly stringent conditions to a nucleotide sequence of SEQ ID NO:1, SEQ ID NO:5, or a complement thereof, which may be the full-length complement thereof; thereby treating or preventing infection in the subject. In another aspect, the method comprises administering to the subject an antigen encoded by an astrovirus, wherein the antigen comprises an amino acid sequence selected from the group consisting of SEQ ID NO:2, SEQ ID NO:3, SEQ ID NO:4, SEQ ID NO:6, SEQ ID NO:7, SEQ ID NO:8; thereby treating or preventing infection in the subject.

In yet another embodiment of the present invention, there is provided a vaccine for the at least partial prevention of gastrointestinal infections in a subject. In one aspect, the vaccine comprises an astrovirus or at least one astrovirus antigen from the astrovirus which induces a gastrointestinal tract infection in a subject and a pharmacologically acceptable carrier wherein the astrovirus has gastrointestinal tract infection inducing characteristics. In one aspect, the astrovirus antigen comprises a protein encoded by a nucleotide sequence of SEQ ID NO:1 or SEQ ID NO:5. In another aspect, the astrovirus antigen has an amino acid sequence selected from the group consisting of SEQ ID NO:2, SEQ ID NO:3, SEQ ID NO:4, SEQ ID NO:6, SEQ ID NO:7, SEQ ID NO:8. In one aspect, the virus of the vaccine is in a killed form. In another aspect, the virus of the vaccine is in a live but attenuated form.

In another embodiment of the invention, there is provided a method for detecting and serotyping astrovirus in a sample. In one aspect, the method comprises (a) contacting a first portion of the sample with a first pair of primers in a first amplification protocol, wherein the first pair of primers have an associated first characteristic amplification product if an astrovirus is present in the sample; (b) determining whether or not the first characteristic amplification product is present; (c) contacting a second portion of the sample with a second pair of primers in a second amplification protocol, wherein the second pair of primers have an associated second characteristic amplification product if an astrovirus is present in the sample and wherein the second pair of primers are different from the first pair of primers; (d) determining whether or not the second characteristic amplification product is present; (e) based on whether or not the first and second characteristic amplification product are present, selecting one or more subsequent pair of primers and contacting the one or more subsequent pair of primers with additional portions of the sample in subsequent amplification protocols, wherein each subsequent pair of primers is different from each pair of primers already used and wherein each subsequent pair of primers has an associated subsequent characteristic amplification product if an astrovirus is present in the sample; (f) determining whether or not the associated characteristic amplification product for each subsequent pair of primers used is present; (g) repeating steps (e) and (f) for one or more subsequent pairs of primers if the astrovirus cannot be serotyped based on the determinations of steps (b), (d), and (f) until the astrovirus can be serotyped, wherein the one or more subsequent pairs of primers are different from all pairs of primers used in earlier amplification protocols; and (h) determining the serotype or groups of serotypes of the astrovirus that may be present in the sample.

In one aspect of the method for detecting and serotyping astrovirus, the astrovirus has a genome comprising a nucleic acid sequence of SEQ ID NO:1, SEQ ID NO:5, or a complement thereof, which may be the full-length complement thereof. In another aspect, the astrovirus has a genome comprising a nucleic acid sequence encoding an amino acid sequence selected from the group consisting of SEQ ID NO:2, SEQ ID NO:3, SEQ ID NO:4, SEQ ID NO:6, SEQ ID NO:7, and SEQ ID NO:8. In one aspect, the first, second, and any subsequent amplification protocols are selected from the group consisting of polymerase chain reactions and reverse-transcription polymerase chain reactions. In one aspect, the first, second, and any subsequent amplification protocols are polymerase chain reactions or reverse-transcription polymerase chain reactions. In another aspect, detecting and serotyping of the astrovirus in the sample is used to diagnose a viral disease or medical condition. In yet another aspect, the viral disease or medical condition is a gastrointestinal tract infection. In one aspect, the sample is a biological sample. In another aspect, the sample is whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, semen, cerebrospinal fluid, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected subject.

In still another embodiment of the invention, there is provided a method for detecting the presence of an astrovirus in a sample. In one aspect, the method comprises: (a) purifying RNA contained in the sample; (b) reverse transcribing the RNA with primers effective to reverse transcribe astrovirus RNA to provide a cDNA; (c) contacting at least a portion of the cDNA with (i) a composition that promotes amplification of a nucleic acid and (ii) an oligonucleotide mixture wherein the mixture comprises at least one oligonucleotide that hybridizes to a highly conserved sequence of the sense strand of an astrovirus nucleic acid and at least one oligonucleotide that hybridizes to a highly conserved sequence of the antisense strand of an astrovirus nucleic acid; (d) carrying out an amplification procedure on the amplification mixture such that, if an astrovirus is present in the sample, an astrovirus amplicon is produced whose sequence comprises a nucleotide sequence of at least a portion of the astrovirus genome; and (e) detecting whether an amplicon is present; wherein the presence of the amplicon indicates that an astrovirus is present in the sample.

In one aspect of the method detecting the presence of an astrovirus, the astrovirus has a genome comprising a nucleic acid sequence of SEQ ID NO:1, SEQ ID NO:5, or a complement thereof, which may be the full-length complement thereof. In another aspect, the astrovirus has a genome comprising a nucleic acid sequence encoding an amino acid sequence selected from the group consisting of SEQ ID NO:2, SEQ ID NO:3, SEQ ID NO:4, SEQ ID NO:6, SEQ ID NO:7, and SEQ ID NO:8. In another aspect, detecting and serotyping of the astrovirus in the sample is used to diagnose a viral disease or medical condition. In yet another aspect, the viral disease or medical condition is a gastrointestinal tract infection. In one aspect, the amplification procedure comprises a polymerase chain reaction. In another aspect, the sample is chosen from the group consisting of whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, semen, cerebrospinal fluid, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected subject. In another aspect, the detection is carried out by a procedure chosen from the group consisting of gel electrophoresis and visualization of amplicons contained in a resulting gel, size separation matrix, capillary electrophoresis and detection of the emerging amplicon, probing for the presence of the amplicon using a labeled probe, sequencing the amplicon, and labeling a PCR primer employed in the method and detecting the label.

In still another embodiment of the invention, there is provided a vaccine for protecting a subject from infection by an astrovirus, wherein the vaccine is selected from the group consisting of: (a) a genetically modified astrovirus encoded by any of the isolated polynucleotide molecule described above; and (b) a viral vector comprising any of the isolated polynucleotide molecule described above; wherein the vaccine is in an amount effective to produce immunoprotection against infection by an astrovirus and the vaccine comprises a vaccine carrier acceptable for human or veterinary use.

In still another embodiment of the invention, there is provided a method of protecting a subject from infection with a strain of astrovirus comprising administering to the subject, an immunogenically protective amount of any of the vaccine described above, thereby stimulating an immunoprotective response against astrovirus in the subject. In one aspect, the subject is a mammal or a bird. In another aspect, the subject is selected from the group consisting of human, pig, cow, sheep, goat, chicken, and duck. In one aspect, the subject is a pig. In another aspect, the bird is a chicken.

In still another embodiment of the invention, there is provided a composition comprising a pharmaceutically acceptable vehicle and at least one astrovirus immunogen selected from the group consisting of an inactivated immunogenic astrovirus, an attenuated immunogenic astrovirus, and an isolated immunogenic astrovirus polypeptide.

In still another embodiment of the invention, there is provided a method of treating or preventing an astrovirus-associated disease or disorder in a subject comprising administering to the subject a therapeutically effective amount of any composition described above. In one aspect, the astrovirus-associated disease or disorder is a gastrointestinal tract infection. In another aspect, the subject is selected from the group consisting of human, pig, cow, sheep, goat, chicken, and duck.

BRIEF DESCRIPTION OF THE DRAWINGS

FIG. 2 shows phylogenetic relationship of HMOAstV species and other astroviruses.

DETAILED DESCRIPTION OF THE INVENTION

Figure 1:
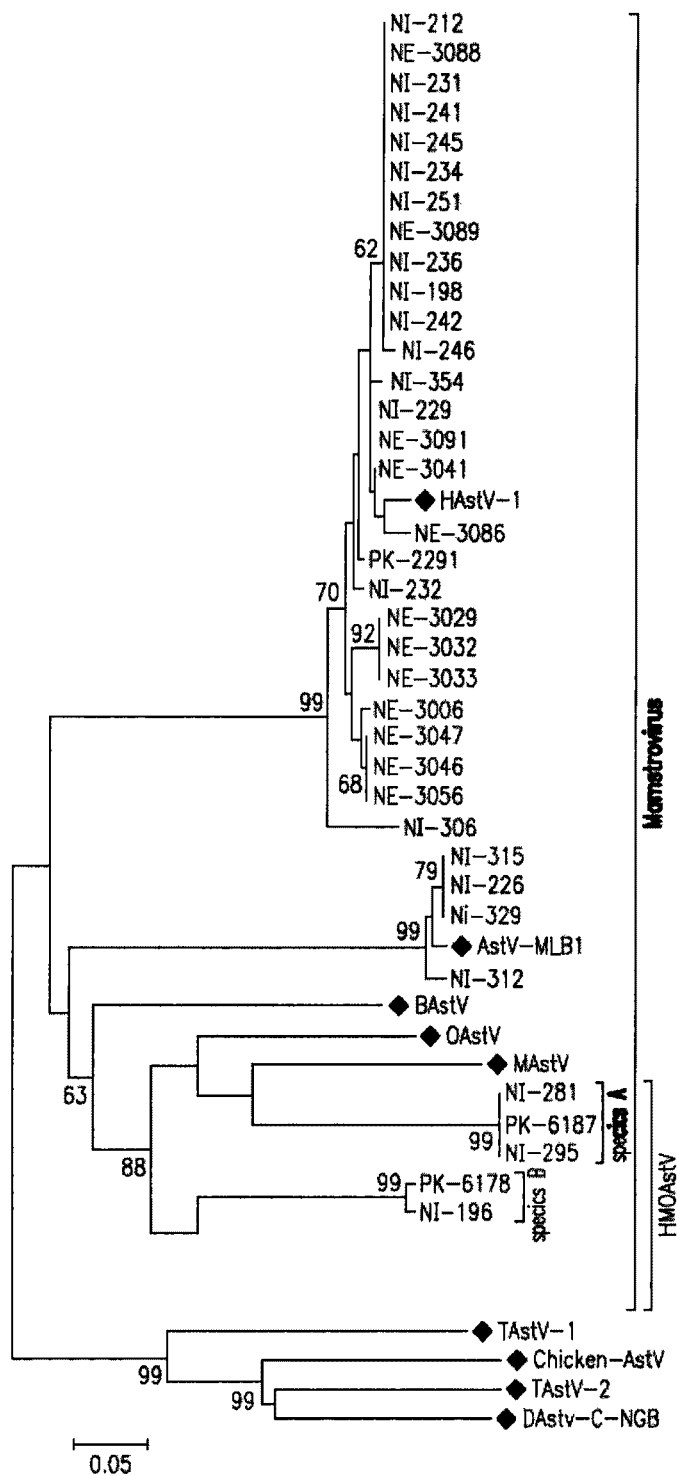
FIG. 1 shows phylogenetic analysis of partial RdRp protein sequence of astroviruses detected in human stool using pan-astrovirus PCR (region corresponds to amino acid position 1192 to 1312 of ORF1ab of the reference HAstV-1 genome NC_001943, protein ID NP_059443). A representative of each astrovirus species belonging to mammalian *Mamastrovirus* and avian *Avastrovirus* genus are used as references. Tree is constructed by using the neighbor-joining method using amino acid pdistances as implemented in MEGA4. The different species of HMOAstV are indicated by brackets. Reference sequences are labeled with diamonds. Bootstrap values >60% are shown in the branches.

The present invention is based on the discovery of novel virus species, HMOAstV-A and HMOAstV-B, which are associated with gastrointestinal tract infections. There are various molecular methods for discovery of novel human viruses including immunoreactive cDNA expression library screening, representational difference analysis (RDA), DNA microarrays and use of degenerate PCR primers. Other methods include sequence independent single primer amplification of nucleic acids in serum (DNase-SISPA), or "metagenomics shotgun sequencing." For these approaches, DNA can be isolated directly from environmental samples and sequenced, without attempting to culture the organisms from which it comes. The DNase-SISPA method first removes contaminating human DNA in plasma or serum by DNase digestion. Viral nucleic acids protected from DNase digestion by their viral coats are then converted into double stranded DNA (dsDNA) using random primers. The dsDNA is then digested by a four base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using Basic Local Alignment Search Tool (BLAST)n (for nucleic acid similarity) and tBLASTx (for protein similarity). The DNase-SISPA method does not require foreknowledge of the viral sequences being amplified and can therefore theoretically amplify more divergent members of known viral families than nucleic acid sequence similarity-dependent approaches using degenerate primers or microarrays.

Accordingly, the present invention provides two new human astrovirus HMOAstV-A and HMOAstV-B and variants thereof, as well as their genomic sequences and the viral proteins encoded thereby. The genome encodes the structural proteins of the virus and non-structural proteins involved in viral replication. The exemplary genomic sequence of HMOAstV-A1 is disclosed as SEQ ID NO:1 and the exemplary genomic sequences of HMOAstV-B1 is disclosed as SEQ ID NO:5. Exemplary amino acid sequences encoded by HMOAstV-A1 ORF1a, ORF1ab, and ORF2 are disclosed as SEQ ID NO:2, SEQ ID NO:3, and SEQ ID NO:4, respectively. Exemplary amino acid sequences encoded by HMOAstV-B1 ORF1a, ORF1ab, and ORF2 are disclosed as SEQ ID NO:6, SEQ ID NO:7, and SEQ ID NO:8, respectively.

The identifications of HMOAstV-A and HMOAstV-B provide methods of detecting the virus, its genome, transcripts, and proteins including structural and non-structural proteins. Antibodies (polyclonal and monoclonal) made to antigens from any of these viral proteins can be used to detect the antigen or protein as well as to isolate the antigens and to remove virus, proteins, or nucleic acids from a sample, e.g., a blood sample. Antibodies to astrovirus antigens can be used in diagnostic assays to detect viral infection. Any suitable sample, including blood, saliva, sputum, etc., can be used in a diagnostic assay of the invention. Such antibodies can also be used in therapeutic applications to inhibit or prevent viral infection.

The astrovirus antigens of the invention can also be used in diagnostic application to detect anti-astrovirus antigen antibodies in infected or exposed subjects. Astrovirus antigens of the invention can also be used therapeutically, as prophylactic vaccines or vaccines for acute or latent infections, e.g., whole virus vaccines, protein or subunit vaccines, and nucleic acid vaccines encoding viral proteins, ORFs or genomes for intracellular expression and secretion or cell surface display, or can be targeted to specific cell types using promoters and vectors.

The astrovirus virus, nucleic acids and proteins of the invention can be used to assay for antiviral compounds, including compounds that inhibit (1) viral interactions at the cell surface, e.g., viral transduction (e.g., block viral cell receptor binding or internalization); (2) viral replication and gene expression, e.g., viral replication (e.g., by inhibiting non-structural protein activity, origin activity, or primer binding), viral transcription (promoter or splicing inhibition, non-structural protein inhibition), viral protein translation, protein processing (e.g., cleavage or phosphorylation); and (3) viral assembly and egress, e.g., viral packaging, and virus release.

"Astrovirus" refers to both the genetic components of the virus, e.g., the genome (positive or negative) and RNA transcripts thereof (either sense or antisense), proteins encoded by the genome (including structural and nonstructural proteins), and viral particles. This description includes astrovirus nucleic acids, alleles, mutants, and interspecies homologs that: (1) have a nucleotide sequence that has greater than about 75% nucleotide sequence identity, 80%, 85%, 90%, preferably 91%, 92%, 93%, 94%, 95%, 96%, 97%, 98% or 99% or greater nucleotide sequence identity, preferably over a region of at least about 25, 50, 100, 200, 500, 1000, or more nucleotides, up to the full length sequence, to the nucleotide sequence as set forth in SEQ ID NO:1, SEQ ID NO:5, or a complement thereof, which may be the full-length complement thereof; (2) encode a protein that binds to antibodies, e.g., polyclonal or monoclonal antibodies, raised against an antigen or an immunogen from an amino acid sequence of a protein encoded by an open reading frame of SEQ ID NO:1 or SEQ ID NO:5; (3) specifically hybridize under stringent hybridization conditions to a nucleic acid sequence as set forth in SEQ ID NO:1, SEQ ID NO:5, or a complement thereof, which may be the full-length complement thereof; (4) encodes a protein having an amino acid sequence that has greater than about 80% identity, 85%, 90%, preferably 91%, 92%, 93%, 94%, 95%, 96%, 97%, 98% or 99% or greater sequence identity, preferably over a region of over a region of at least about 25, 50, 100, 200, 500, 1000, or more amino acids, to a protein as set forth in SEQ ID NO:2, SEQ ID NO:3, SEQ ID NO:4, SEQ ID NO:6, SEQ ID NO:7, or SEQ ID NO:8. Astrovirus nucleic acids may be isolated from a host including, but not limited to, primate, e.g., human; rodent, e.g., rat, mouse, hamster; cow, pig, horse, sheep, or any mammal. The nucleic acids and proteins of the invention include both naturally occurring and recombinant molecules.

Disclosed astrovirus nucleic acids can be used to produce infectious clones, e.g., for production of recombinant viral particles, including empty capsids or capsids containing a recombinant (e.g., wild type or further comprising a heterologous nucleic acid) or modified (e.g., mutated) astrovirus genome, which may be replication competent or incompetent, using the methods disclosed in U.S. Pat. Nos. 6,558,676; 6,132,732; 6,001,371; 5,916,563; 5,827,647; 5,508,186; 6,379,885; 6,287,815; 6,204,044; and 5,449,608. Such particles are useful as gene transfer vehicles, and as vaccines, and for use in diagnostic applications and for drug discovery assays for antiviral compounds, as discussed below.

"Protein encoded by astrovirus" or "protein encoded by astrovirus open reading frame (ORF)" refers to structural and non-structural astrovirus proteins that: (1) are encoded by a nucleic acid molecule of the invention such as a nucleic acid molecule that has greater than about 75% nucleotide sequence identity, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleotides, up to the full length sequence, to the nucleotide sequence as set forth in SEQ ID NO:1, SEQ ID NO:5, or a complement thereof, which may be the full-length complement thereof; (2) bind to antibodies, e.g., polyclonal or monoclonal antibodies, raised against an immunogen comprising an amino acid sequence of a protein as set forth in SEQ ID NO:2, SEQ ID NO:3, SEQ ID NO:4, SEQ ID NO:6, SEQ ID NO:7, SEQ ID NO:8, or conservatively modified variants thereof; (3) is encoded by a nucleic acid molecule that specifically hybridizes under stringent hybridization conditions to a nucleic acid sequence as set forth in SEQ ID NO:1, SEQ ID NO:5, or a complement thereof, which may be the full-length complement thereof, (for example, an open reading frame starting with an ATG and ending with a stop codon); (4) have an amino acid sequence that has greater than about 80% identity, 85%, 90%, preferably 91%, 92%, 93%, 94%, 95%, 96%, 97%, 98% or 99% or greater identity, preferably over a region of at least about 25, 50, 100, 200, 500, 1000, or more amino acids, to a protein as set forth in SEQ ID NO:2, SEQ ID NO:3, SEQ ID NO:4, SEQ ID NO:6, SEQ ID NO:7, SEQ ID NO:8, or conservatively modified variants thereof.

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from an eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 75% identity, preferably 80%, 85%, 90%, 91%, 92%, 93%, 94%, 95%, 96%, 97%, 98%, 99%, or higher identity over a specified region (e.g., nucleotide sequence or amino acid sequence corresponding to SEQ ID NO:1 and SEQ ID NO:2, respectively), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

There are several methods available and well known to those skilled in the art to obtain full-length DNAs, or extend short DNAs, for example those based on the method of Rapid Amplification of cDNA Ends (RACE). Another sequencing method is based on detecting the activity of DNA polymerase with a chemiluminescent enzyme. Essentially, the method allows sequencing of a single strand of DNA by synthesizing the complementary strand along it, one base pair at a time, and detecting which base was actually added at each step. The template DNA is immobilized, and solutions of A, C, G, and T nucleotides are added sequentially. Light is produced only when the nucleotide solution compliments the first unpaired base of the template. The sequence of solutions which produce chemiluminescent signals allows the determination of the sequence of the template.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, by computerized implementations of these algorithms (GAP, BESTFIT, FASTA, and TFASTA in the Wisconsin Genetics Software Package (Genetics Computer Group, 575 Science Dr., Madison, Wis.), or by manual alignment and visual inspection (see, e.g., *Current Protocols in Molecular Biology*, Ausubel et al., eds. (New York, Wiley 1994, and 1995 supplement).

A preferred example of algorithm that is suitable for determining percent sequence identity and sequence similarity are the BLAST and BLAST 2.0 algorithms, which are described in Altschul et al. (1977) *Nuc. Acids Res.* 25:3389-3402 and Altschul et al. (1990) *J. Mol. Biol.* 215:403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10 $\mu$M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff (1989) *Proc. Natl. Acad. Sci. USA* 89:10915) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, Ausubel et al., eds. (New York, Wiley 1994).

For polymerase chain reactions or PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, see e.g., Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al. (1990) *Nature* 348:552-554).

For preparation of antibodies, e.g., recombinant, monoclonal, or polyclonal antibodies, many technique known in the art can be used (see, e.g., Kohler & Milstein (1975) *Nature* 256:495-497; Kozbor et al. (1983) *Immunology Today* 4: 72; Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778 and 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016; Marks et al. (1992) *Bio/Technology* 10:779-783; Lonberg et al. (1994) *Nature* 368:856-859; Morrison (1994) *Nature* 368:812-13; Fishwild et al. (1996) *Nature Biotechnology* 14:845-51; Neuberger (1996) *Nature Biotechnology* 14:826; and Lonberg & Huszar (1995) *Intern. Rev. Immunol.* 13:65-93). Alternatively, phage display technology can be used to identify antibodies and heteromeric Fab fragments that specifically bind to selected antigens (see, e.g., McCafferty et al. (1990) *Nature* 348:552-554; Marks et al. (1992) *Biotechnology* 10:779-783). Antibodies can also be made bispecific, i.e., able to recognize two different antigens (see, e.g., WO 93/08829, Traunecker et al. (1991) *EMBO J.* 10:3655-3659; and Suresh et al. (1986) *Methods in Enzymology* 121:210). Antibodies can also be heteroconjugates, e.g., two covalently joined antibodies, or immunotoxins (see, e.g., U.S. Pat. No. 4,676,980; WO 91/00360; and WO 92/200373).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al. (1986) *Nature* 321:522-525; Riechmann et al. (1988) *Nature* 332:323-327; Verhoeyen et al. (1988) *Science* 239:1534-1536; and Presta (1992) *Curr. Op. Struct. Biol.* 2:593-596), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The antibody can be conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to an astrovirus, polymorphic variants, alleles, orthologs, and conservatively modified variants, or splice variants, or portions thereof, can be selected to obtain only those polyclonal antibodies that are specifically immunoreactive with astrovirus and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

The phrase "functional effects" in the context of assays for testing compounds that modulate activity of an astrovirus includes the determination of a parameter that is indirectly or directly under the influence of an astrovirus, e.g., a phenotypic or chemical effect, such as the ability to increase or decrease viral genome replication, viral RNA and protein production, virus packaging, viral particle production (particularly replication competent viral particle production), cell receptor binding, viral transduction, cellular infection, antibody binding, inducing a cellular or humoral immune response, viral protein enzymatic activity, etc. "Functional effects" include in vitro, in vivo, and ex vivo activities. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for a protein; measuring inducible markers or transcriptional activation of a protein; measuring binding activity or binding assays, e.g., binding to antibodies; measuring changes in ligand or substrate binding activity; measuring viral replication; measuring cell surface marker expression; measurement of changes in protein levels; measurement of RNA stability; identification of downstream or reporter gene expression (CAT, luciferase, β-gal, GFP and the like), e.g., via chemiluminescence, fluorescence, colorimetric reactions, antibody binding, and inducible markers.

"Inhibitors," "activators," and "modulators" of astrovirus nucleic acid and polypeptide sequences are used to refer to activating, inhibitory, or modulating molecules identified using in vitro and in vivo assays of the astrovirus nucleic acid and polypeptide sequences. Inhibitors are compounds that, e.g., bind to, partially or totally block activity, decrease, prevent, delay activation, inactivate, desensitize, or down regulate the activity or expression of astrovirus, e.g., antagonists.

"Activators" are compounds that increase, open, activate, facilitate, enhance activation, sensitize, agonize, or up regulate astrovirus activity, e.g., agonists. Inhibitors, activators, or modulators also include genetically modified versions of astrovirus, e.g., versions with altered activity, as well as naturally occurring and synthetic ligands, substrates, antagonists, agonists, antibodies, peptides, cyclic peptides, nucleic acids, antisense molecules, ribozymes, small chemical molecules and the like. Such assays for inhibitors and activators include, e.g., expressing astrovirus in vitro, in cells, or cell membranes, applying putative modulator compounds, and then determining the functional effects on activity, as described above.

Samples or assays comprising astrovirus that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of astrovirus can be achieved when the activity value relative to the control is about 80%, preferably 50%, more preferably 25-0%. Activation of astrovirus can be achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

An "siRNA" molecule or an "RNAi" molecule refers to a nucleic acid that forms a double stranded RNA, which double stranded RNA has the ability to reduce or inhibit expression of a gene or target gene when the siRNA expressed in the same cell as the gene or target gene. The term "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA.

The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also WO 2003/076592, herein incorporated by reference in its entirety.

An siRNA molecule or RNAi molecule is "specific" for a target nucleic acid if it reduces expression of the nucleic acid by at least about 10% when the siRNA or RNAi is expressed in a cell that expresses the target nucleic acid.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology*, Ausubel et al., eds. (New York, Wiley 1994).

Astrovirus, polymorphic variants, orthologs, and alleles that are substantially identical to an amino acid sequence encoded by nucleic acids of SEQ ID NO:1 or SEQ ID NO:5 can be isolated using nucleic acid probes and oligonucleotides under stringent hybridization conditions, by screening DNA libraries or by using PCR. Genes encoding astrovirus proteins can be isolated using cDNA libraries. Alternatively, expression libraries can be used to clone the astrovirus, polymorphic variants, orthologs, and alleles by detecting expressed homologs immunologically with antisera or purified antibodies made against astrovirus or portions thereof.

Other techniques that can be used to identify known and previously uncharacterized astrovirus isolates, including representational difference analysis (RDA), DNA microarrays and use of degenerate PCR primers or other methods well known to those of skill in the art. Other methods for determining the sequence of an astrovirus include, for example, sequence independent single primer amplification of nucleic acids in serum (DNase-SISPA). In this method, DNA is isolated directly from environmental samples and sequenced. This method first removes contaminating human DNA in plasma or serum by DNase digestion. Viral nucleic acids protected from DNase digestion by their viral coats are then converted into double stranded DNA (dsDNA) using random primers. The dsDNA is then digested by a 4 base pair specific restriction endonuclease resulting in two overhanging bases to which are ligated a complementary oligonucleotide linker. A PCR primer complementary to the ligated linker is then used to PCR amplify the sequences between the restriction sites. The PCR products are analyzed by PAGE and distinct DNA bands are extracted, subcloned and sequenced. Similarity to known viruses is then tested using BLASTn (for nucleic acid similarity) and tBLASTx (for protein similarity). The DNase-SISPA method does not require foreknowledge of the viral sequences being amplified and can therefore theoretically amplify more divergent members of known viral families than nucleic acid sequence similarity-dependent approaches using degenerate primers or microarrays. There are several methods available and well known to those skilled in the art to obtain full-length DNAs, or extend short DNAs, for example, those based on the method of Rapid Amplification of cDNA Ends (RACE) and large scale sequencing.

To make a cDNA library to clone astrovirus genes expressed by the genome, the source used should be rich in the RNA of choice. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman (1983) *Gene* 25:263-269; Sambrook et al., supra; Ausubel et al., supra).

For a genomic library, the DNA is extracted from the tissue and optionally mechanically sheared or enzymatically digested. The fragments are then separated by gradient centrifugation from undesired sizes and are constructed in suitable vectors. These vectors are packaged in vitro. Recombinant vectors can be analyzed, e.g., by plaque hybridization as described in Benton & Davis (1977) *Science* 196:180-182. Colony hybridization is carried out as generally described in Grunstein et al. (1975) *Proc. Natl. Acad. Sci. USA.*, 72:3961-3965.

A preferred method of isolating astrovirus and orthologs, alleles, mutants, polymorphic variants, splice variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR and RT-PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Astrovirus encoding mRNA in physiological samples, for nucleic acid sequencing, or for other purposes. Genes amplified by the PCR reaction can be purified from agarose gels and cloned into an appropriate vector.

Gene expression of astroviruses can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding an astrovirus genome or protein can be used with high density oligonucleotide array technology to identify astrovirus, orthologs, alleles, conservatively modified variants, and polymorphic variants in this invention. In the case where the homologs being identified are linked to modulation of the cell cycle, they can be used with oligonucleotide array as a diagnostic tool in detecting the disease in a biological sample, see, e.g., Gunthand et al. (1998) *AIDS Res. Hum. Retroviruses* 14: 869-876; Kozal et al. (1996) *Nat. Med.* 2:753-759; Matson et al. (1995) *Anal. Biochem.* 224: 110-106; Lockhart et al. (1996) *Nat. Biotechnol.* 14:1675-1680; Gingeras et al. (1998) *Genome Res.* 8:435-448; Hacia et al. (1998) *Nucleic Acids Res.* 26:3865-3866.

The gene of choice is typically cloned into intermediate vectors before transformation into prokaryotic or eukaryotic cells for replication and/or expression. These intermediate vectors are typically prokaryote vectors, e.g., plasmids, or shuttle vectors.

To obtain high level expression of a cloned gene or genome, one typically subclones the nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al. (1983) *Gene* 22:229-235; Mosbach et al. (1983) *Nature* 302:543-545. Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard (1992) *PNAS* 89:5547; Oligino et al. (1998) *Gene Ther.* 5:491-496; Wang et al. (1997) *Gene Ther.* 4:432-441; Neering et al. (1996) *Blood* 88:1147-1155; and Rendahl et al. (1998) *Nat. Biotechnol.* 16:757-761). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical; any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al. (1989) *J. Biol. Chem.* 264:17619-17622; *Guide to Protein Purification*, in Methods in Enzymology, vol. 182 (Deutscher, ed., 1990)). Transformation of eukaryotic and prokaryotic cells are performed according to standard techniques (see, e.g., Morrison (1977) *J. Bact.* 132:349-351; Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing astrovirus proteins and nucleic acids.

After the expression vector is introduced into the cells, the transfected cells are cultured under conditions favoring expression of the protein of choice, which is recovered from the culture using standard techniques identified below.

Either naturally occurring or recombinant astrovirus proteins can be purified for use in diagnostic assays, for making antibodies (for diagnosis and therapy) and vaccines, and for assaying for anti-viral compounds. Exemplary astrovirus protein sequences are disclosed as SEQ ID NO:2, SEQ ID NO:3, SEQ ID NO:4, SEQ ID NO:6, SEQ ID NO:7, and SEQ ID NO:8. Naturally occurring proteins can be purified, e.g., from human tissue samples. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes,

*Protein Purification: Principles and Practice* (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

Methods for production and purification of recombinant protein from a bacterial or eukaryotic (e.g., yeast, mammalian cell, and the like) system are well known in the art. Recombinant proteins are expressed by transformed host cells, (e.g., bacteria) in large amounts, typically after promoter induction; but expression can be constitutive. Promoter induction with IPTG is one example of an inducible promoter system. Host cells are grown according to standard procedures in the art. Where the host cell is a bacterial cell, fresh or frozen bacteria cells are used for isolation of protein.

Recombinant proteins, particularly when expressed in bacterial host cells, may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM Tris/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, where the host cell is a bacterium, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard protein separation techniques for purifying proteins are also contemplated in the present invention. Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In addition to the detection of an astrovirus gene and gene expression using nucleic acid hybridization technology, one can also use immunoassays to detect astrovirus proteins, virus, and nucleic acids of the invention. Such assays are useful for, e.g., therapeutic and diagnostic applications. Immunoassays can be used to qualitatively or quantitatively analyze protein, virus, and nucleic acids. A general overview of the applicable technology can be found in Harlow & Lane, *Antibodies: A Laboratory Manual* (1988).

Methods of producing polyclonal and monoclonal antibodies that react specifically with astrovirus protein, virus and nucleic acids are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein (1975) *Nature* 256:495-497). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al. (1989) *Science* 246:1275-1281; Ward et al. (1989) *Nature* 341:544-546).

A number of immunogens comprising portions of an astrovirus protein, virus or nucleic acid may be used to produce antibodies specifically reactive with the astrovirus. For example, a recombinant astrovirus protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into a subject capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The immune response to the immunogen preparation is monitored by taking test bleeds and determining the titer of reactivity to the beta subunits. When appropriately high titers of antibody to the immunogen are obtained, blood is collected and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from a subject immunized with a desired antigen are immortalized, commonly by fusion with a myeloma cell (see, Kohler & Milstein (1976) *Eur. J. Immunol.* 6:511-519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275-1281.

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-astrovirus proteins and nucleic acids, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular astrovirus protein can also be made by subtracting out other cross-reacting proteins, e.g., from other human astroviruses or other non-human astroviruses. In this manner, antibodies that bind only to the protein of choice may be obtained.

Once the specific antibodies against an astrovirus protein, virus or nucleic acid in are available, the antigen can be detected by a variety of immunoassay methods. In addition, the antibody can be used therapeutically. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in Enzyme Immunoassay (Maggio, ed., 1980); and Harlow & Lane, supra.

Protein, in this case astrovirus protein which is either associated with or separate from an astrovirus viral particle, can be detected and/or quantified using any of a number of well recognized immunological binding assays (see, e.g., U.S. Pat. Nos. 4,366,241; 4,376,110; 4,517,288; and 4,837,168). Astrovirus viral particles may be detected based on an epitope defined by the viral proteins as presented in a viral particle and/or an epitope defined by a viral protein that is separate from a viral particle (e.g., such as may be present in an infected cell). As used in this context, "antigen" is meant to refer to an astrovirus polypeptide as well as astrovirus viral particles. For a review of the general immunoassays, see also *Methods in Cell Biology: Antibodies in Cell Biology*, volume 37 (Asci, ed. 1993); *Basic and Clinical Immunology* (Stites & Terr, eds., 7th ed. 1991). Immunological binding assays (or immunoassays) typically use an antibody that specifically binds to a protein or antigen of choice. The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled astrovirus protein nucleic acid or a labeled anti-astrovirus antibody. Alternatively, the labeling agent may be a third moiety, such a secondary antibody, which specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al. (1973) *J. Immunol.* 111:1401-1406; Akerstrom et al. (1985) *J. Immunol.* 135:2589-2542). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Immunoassays for detecting astrovirus protein, virus and nucleic acid in samples may be either competitive or noncompetitive, and may be either quantitative or non-quantitative. Noncompetitive immunoassays are assays in which antigen is directly detected and, in some instances the amount of antigen directly measured. In a "sandwich" assay, for example, the anti-astrovirus antibodies can be bound directly to a solid substrate on which they are immobilized. These immobilized antibodies then capture the astrovirus antigen present in the test sample. Proteins thus immobilized are then bound by a labeling agent, such as a second anti-astrovirus antigen antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, astrovirus antigen present in a sample is detected indirectly by detecting a decrease in a detectable signal associated with a known, added (exogenous) astrovirus antigen displaced (competed away) from an anti-astrovirus antigen antibody by the unknown astrovirus antigen present in a sample. In this manner, such assays can also be adapted to provide for an indirect measurement of the amount of astrovirus antigen present in the sample. In one competitive assay, a known amount of astrovirus antigen is added to a sample and the sample is then contacted with an antibody that specifically binds to the astrovirus antigen. The amount of exogenous astrovirus antigen bound to the antibody is inversely proportional to the concentration of astrovirus antigen present in the sample. In a particularly preferred embodiment, the antibody is immobilized on a solid substrate. The amount of astrovirus antigen bound to the antibody may be determined either by measuring the amount of astrovirus antigen present in astrovirus antigen/antibody complex, or alternatively by measuring the amount of remaining uncomplexed protein. The amount of astrovirus antigen may be detected by providing a labeled astrovirus antigen.

A hapten inhibition assay is another competitive assay. In this assay the known astrovirus antigen is immobilized on a solid substrate. A known amount of anti-astrovirus antigen antibody is added to the sample, and the sample is then contacted with the immobilized astrovirus antigen. The amount of anti-astrovirus antigen bound to the known immobilized astrovirus antigen is inversely proportional to the amount of astrovirus antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can also be used for crossreactivity determinations. For example, an astrovirus antigen can be immobilized to a solid support. Proteins are added to the assay that compete for binding of the antisera to the immobilized antigen. The ability of the added proteins to compete for binding of the antisera to the immobilized protein is compared to the ability of the astrovirus antigen to compete with itself The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an astrovirus antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the astrovirus antigen that is required to inhibit 50% of binding, then the second protein is said to specifically bind to the polyclonal antibodies generated to astrovirus antigen.

Western blot (immunoblot) analysis can be used to detect and quantify the presence of astrovirus antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the astrovirus antigen. The anti-astrovirus antigen antibodies specifically bind to the astrovirus antigen on the solid support. These antibodies may be directly labeled or alternatively may be subsequently detected using labeled antibodies (e.g., labeled sheep anti-mouse antibodies) that specifically bind to the anti-astrovirus antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al. (1986) *Amer. Clin. Prod. Rev.* 5:34-41).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize astrovirus antigen, or secondary antibodies that recognize anti-astrovirus antigen.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

The present invention provides diagnostic assays to detect astrovirus, astrovirus nucleic acids (genome and genes), astrovirus antibodies in an infected subject, and astrovirus proteins. In one embodiment, astrovirus nucleic acids are detected using a nucleic acid amplification-based assay, such as a PCR assay, e.g., in a quantitative assay to determine viral load. In another embodiment, astrovirus antigens are detected using a serological assay with antibodies (either monoclonal or polyclonal) to antigens encoded by astroviruses.

In one embodiment of the present invention, the presence of astrovirus, astrovirus nucleic acid, or astrovirus protein in a sample is determined by an immunoassay. Enzyme mediated immunoassays such as immunofluorescence assays (IFA), enzyme linked immunosorbent assays (ELISA) and immunoblotting (western) assays can be readily adapted to accomplish the detection of the astrovirus or astrovirus proteins. An ELISA method effective for the detection of the virus can, for example, be as follows: (1) bind an anti-astrovirus antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an anti-astrovirus antibody in the sample or a specific astrovirus protein as well as the virus.

Another immunologic technique that can be useful in the detection of astroviruses is the competitive inhibition assay, utilizing monoclonal antibodies (MABs) specifically reactive with the virus. Briefly, serum or other body fluids from the subject is reacted with an antibody bound to a substrate (e.g., an ELISA 96-well plate). Excess serum is thoroughly washed away. A labeled (enzyme-linked, fluorescent, radioactive, etc.) monoclonal antibody is then reacted with the previously reacted astrovirus-antibody complex. The amount of inhibition of monoclonal antibody binding is measured relative to a control. MABs can also be used for detection directly in samples by IFA for MABs specifically reactive for the antibody-virus complex.

Alternatively, an astrovirus antigen and/or a patient's antibodies to the virus can be detected utilizing a capture assay. Briefly, to detect antibodies to astrovirus in a patient sample, antibodies to the patient's immunoglobulin, e.g., anti-IgG (or IgM) are bound to a solid phase substrate and used to capture the patient's immunoglobulin from serum. An astrovirus, or reactive fragments of an astrovirus, can then be contacted with the solid phase followed by addition of a labeled antibody. The amount of patient astrovirus specific antibody can then be quantitated by the amount of labeled antibody binding.

Additionally, a micro-agglutination test can also be used to detect the presence of astrovirus in test samples (see e.g., Constantine and Wreghitt (1991) *J Med. Microbiol.* 34(1):29-31). Briefly, latex beads are coated with an antibody and mixed with a test sample, such that astrovirus in the tissue or body fluids that is specifically reactive with the antibody crosslink with the receptor, causing agglutination. The agglutinated antibody-virus complexes form a precipitate, visible with the naked eye or by spectrophotometer. Other assays include serologic assays, in which the relative concentrations of IgG and IgM are measured.

In the diagnostic methods described above, the sample can be taken directly from the patient or in a partially purified form. The antibody specific for a particular astrovirus (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

The detectable moiety can allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (see e.g., Harlow and Lane (1988) *Antibodies: A Laboratory Manual*, Cold Spring Harbor Press).

As described herein, an astrovirus infection may also, or alternatively, be detected based on the level of an astrovirus RNA or DNA in a biological sample. Primers from astrovirus sequences can be used for detection of astrovirus, diagnosis, and determination of astrovirus viral load. Any suitable primer can be used to detect the genome, nucleic acid subsequence, ORF, or protein of choice, using, e.g., methods described in U.S. Pat. No. 20030104009. For example, the subject nucleic acid compositions can be used as single- or double-stranded probes or primers for the detection of astrovirus mRNA or cDNA generated from such mRNA, as obtained may be present in a biological sample (e.g., extracts of human cells). The astrovirus polynucleotides of the invention can also be used to generate additional copies of the polynucleotides, to generate antisense oligonucleotides, and as triple-strand forming oligonucleotides. For example, two oligonucleotide primers may be employed in a polymerase chain reaction (PCR) based assay to amplify a portion of astrovirus cDNA derived from a biological sample, wherein at least one of the oligonucleotide primers is specific for (i.e., hybridizes to) the astrovirus polynucleotide. The amplified cDNA is then separated and detected using techniques well known in the art, such as gel electrophoresis. Similarly, oligonucleotide probes that specifically hybridize to an astrovirus polynucleotide may be used in a hybridization assay to detect the presence of the astrovirus polynucleotide in a biological sample. These and other uses are described in more detail below.

Nucleic acid probes specific to the new astrovirus species of the invention can be generated using the polynucleotide sequences disclosed herein. The probes are preferably at least about 12, 15, 16, 18, 20, 22, 24, or 25 nucleotide fragments of a contiguous sequence of SEQ ID NO:1, SEQ ID NO:5, or a complement thereof, which may be the full-length complement thereof, or other polynucleotide sequence encoding an astrovirus polypeptide. Nucleic acid probes can be less than about 200, 150, 100, 75, 60, 50, 40, 30, or 25 nucleotides in length, or may be up to 2 kb, 1.5 kb, 1 kb, 0.5 kb, 0.25 kb, 0.1 kb, or 0.05 kb in length. Probes may be 5 to 40 nucleotides in length, or 8 to 35 nucleotides, or 10 to 25 nucleotides. The probes can be produced by, for example, chemical synthesis, PCR amplification, generation from longer polynucleotides using restriction enzymes, or other methods well known in the art.

The polynucleotides of the invention, particularly where used as a probe in a diagnostic assay, can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrho-damine (TAMRA)), radioactive labels, (e.g. $^{32}P$, $^{35}S$, and $^{3}H$), and the like. The detectable label can involve two stage systems (e.g., biotin-avidin, hapten-anti-hapten antibody, and the like).

The invention also includes solid substrates, such as arrays, comprising any of the polynucleotides described herein. The polynucleotides are immobilized on the arrays using methods known in the art. An array may have one or more different polynucleotides.

Any suitable qualitative or quantitative methods known in the art for detecting a specific astrovirus nucleic acid (e.g., RNA or DNA) can be used. Astrovirus nucleic acids can be detected by, for example, in situ hybridization in tissue sections, using methods that detect single base pair differences between a hybridizing nucleic acid (e.g., using the technology described in U.S. Pat. No. 5,846,717), by reverse transcriptase-PCR, or in Northern blots containing poly $A^+$ mRNA, and other methods well known in the art. For detection of astrovirus polynucleotides in blood or blood-derived samples, the use of methods that allow for detection of single base pair mismatches is preferred.

Using the astrovirus nucleic acid as a basis, nucleic acid probes (e.g., including oligomers of at least about 8 nucleotides or more) can be prepared, either by excision from recombinant polynucleotides or synthetically, which probes hybridize with the astrovirus nucleic acid, and thus are useful in detection of astrovirus virus in a sample, and identification of infected individuals, as well as further characterization of the viral genome(s). The probes for astrovirus polynucleotides (natural or derived) are of a length or have a sequence which allows the detection of unique viral sequences by hybridization. While about 6-8 nucleotides may be useful, longer sequences may be preferred, e.g., sequences of about 10-12 nucleotides, or about 20 nucleotides or more. Preferably, these sequences will derive from regions which lack heterogeneity among astrovirus viral isolates.

Nucleic acid probes can be prepared using routine methods, including automated oligonucleotide synthetic methods. A complement to any unique portion of the astrovirus genome may be used, e.g., a portion of the astrovirus genome that allows for distinguishing astrovirus from other viruses that may be present in the sample. For use as probes, complete complementarity is desirable, though it may be unnecessary as the length of the fragment is increased.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled with a detectable label. Suitable labels, and methods for labeling probes are known in the art, can include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the astrovirus genome or portion thereof. Therefore, usually high stringency conditions are desirable in order to prevent or at least minimize false positives. However, conditions of high stringency should only be used if the probes are complementary to regions of the viral genome which lack heterogeneity among astrovirus viral isolates. The stringency of hybridization is determined by a number of factors during hybridization and during the washing procedure, including temperature, ionic strength, length of time, and concentration of formamide. These factors are outlined in, for example, Sambrook et al. (1989) *Molecular Cloning; A Laboratory Manual*, Second Edition (Cold Spring Harbor Press, Cold Spring Harbor, N.Y.).

Generally, it is expected that the astrovirus sequences will be present in a biological sample (e.g., blood, cells, and the liked) obtained from an infected individual at relatively low levels, e.g., at approximately $10^2$-$10^4$ astrovirus sequences per $10^6$ cells. This level may require that amplification techniques be used in hybridization assays. Such techniques are known in the art.

For example, the Enzo Biochemical Corporation "Bio-Bridge" system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European application no. EP0,124,221A1 describe a DNA hybridization assay in which: (1)

analyte is annealed to a single-stranded DNA probe that is complementary to an enzyme-labeled oligonucleotide; and (2) the resulting tailed duplex is hybridized to an enzyme-labeled oligonucleotide. EP0,204,510B1 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

Non-PCR-based, sequence specific DNA amplification techniques can also be used in the invention to detect astrovirus sequences. An example of such techniques includes, but is not necessarily limited to the Invader assay, see, e.g., Kwiatkowski et al. (1999) *Mol. Diagn.* 4(4):353-64; U.S. Pat. No. 5,846,717.

A particularly desirable technique may first involve amplification of the target astrovirus sequences in sera approximately 10,000 fold, e.g., to approximately 10 sequences/mL. This may be accomplished, for example, by the polymerase chain reactions (PCR) technique described in Mullis, U.S. Pat. No. 4,683,195, and Mullis et al. U.S. Pat. No. 4,683,202. Other amplification methods are well known in the art. In a preferred embodiment, a sample suspected of comprising the astrovirus nucleic acid is contacted with at least one primer that hybridizes to a nucleotide sequence of SEQ ID NO:1, SEQ ID NO:5, or a complement thereof, which may be the full-length complement thereof, said contacting being under conditions suitable for amplification of an amplification product from an astrovirus nucleic acid in the sample.

The probes, or alternatively nucleic acid from the samples, may be provided in solution for such assays, or may be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, and Protein A beads.

In one embodiment, the probe (or sample nucleic acid) is provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP0,799,897; WO 97/29212; WO 97/27317; EP0,785,280; WO 97/02357; U.S. Pat. Nos. 5,593,839; 5,578,832; EP 728 520; U.S. Pat. No. 5,599,695; EP0,721,016; U.S. Pat. No. 5,556,752; WO 95/22058; and U.S. Pat. No. 5,631,734. Arrays are particularly useful where, for example, a single sample is to be analyzed for the presence of two or more nucleic acid target regions, as the probes for each of the target regions, as well as controls (both positive and negative) can be provided on a single array. Arrays thus facilitate rapid and convenience analysis.

The invention further provides diagnostic reagents and kits comprising one or more such reagents for use in a variety of diagnostic assays, including for example, immunoassays such as ELISA and "sandwich"-type immunoassays, as well as nucleic acid assay, e.g., PCR assays. In a related embodiment, the assay is performed in a flow-through or strip test format, wherein the binding agent is immobilized on a membrane, such as nitrocellulose. Such kits may preferably include at least a first peptide, or a first antibody or antigen binding fragment of the invention, a functional fragment thereof, or a cocktail thereof, or a first oligo pair, and means for signal generation. The kit's components may be pre-attached to a solid support, or may be applied to the surface of a solid support when the kit is used. The signal generating means may come pre-associated with an antibody or nucleic acid of the invention or may require combination with one or more components, e.g., buffers, nucleic acids, antibody-enzyme conjugates, enzyme substrates, or the like, prior to use.

Kits may also include additional reagents, e.g., blocking reagents for reducing nonspecific binding to the solid phase surface, washing reagents, enzyme substrates, enzymes, and the like. The solid phase surface may be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

Assays for modulators of astroviruses are also contemplated in the present invention. Modulation of an astrovirus, and corresponding modulation of the cell cycle or proliferation, can be assessed using a variety of in vitro and in vivo assays, including cell-based models. Such assays can be used to test for inhibitors and activators of astroviruses. Modulators of astroviruses are tested using either recombinant or naturally occurring protein of choice, preferably human astroviruses.

Preferably, the astrovirus will have the sequence as disclosed in SEQ ID NO:1 or SEQ ID NO:5. Alternatively, the astrovirus of the assay will be derived from an eukaryote and encode an amino acid subsequence having substantial amino acid sequence identity to an amino acid sequence selected from the group consisting of SEQ ID NO:2, SEQ ID NO:3, SEQ ID NO:4, SEQ ID NO:6, SEQ ID NO:7, and SEQ ID NO:8. Generally, the amino acid sequence identity will be at least 75%, preferably at least 80%, 85%, or 90%, most preferably at least 95%.

Measurement of modulation of an astrovirus or a cell expressing astrovirus, either recombinant or naturally occurring, can be performed using a variety of assays, in vitro, in vivo, and ex vivo, as described herein. A suitable physical, chemical or phenotypic change that affects activity, e.g., enzymatic activity, cell surface marker expression, viral replication and proliferation can be used to assess the influence of a test compound on the polypeptide of this invention. When the functional effects are determined using intact cells or animals, one can also measure a variety of effects.

Assays to identify compounds with astrovirus modulating activity can be performed in vitro. Such assays can use full length astrovirus or a variant thereof, or a mutant thereof, or a fragment thereof, such as a RING domain. Purified recombinant or naturally occurring protein can be used in the in vitro methods of the invention. In addition to purified astrovirus, the recombinant or naturally occurring protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify astrovirus-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the protein is washed, interference with binding, either of the potential modulator or of the known ligand or substrate, is determined. Often, either the potential modulator or the known ligand or substrate is labeled.

In another embodiment, the astrovirus is expressed in a cell, and functional, e.g., physical and chemical or phenotypic, changes are assayed to identify modulators of the cell cycle. Any suitable functional effect can be measured, as described herein. The astrovirus can be naturally occurring or recombinant. Also, fragments of the astrovirus or chimeric proteins can be used in cell based assays. In addition, point mutants in essential residues required by the catalytic site can be used in these assays.

The compounds tested as modulators of astrovirus can be any small organic molecule, or a biological entity, such as a protein, e.g., an antibody or peptide, a sugar, a nucleic acid, e.g., an antisense oligonucleotide or a ribozyme or RNAi, or a lipid. Alternatively, modulators can be genetically altered versions of an astrovirus. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), and Fluka Chemika-Biochemica Analytika (Buchs Switzerland).

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175; Furka (1991) *Int. J. Pept. Prot. Res.* 37:487-493; and Houghton et al. (1991) *Nature* 354:84-88). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al. (1993) *Proc. Nat. Acad. Sci. USA* 90:6909-6913), vinylogous polypeptides (Hagihara et al. (1992) *J. Amer. Chem. Soc.* 114:6568), non-peptidal peptidomimetics with glucose scaffolding (Hirschmann et al. (1992) *J. Amer. Chem. Soc.* 114:9217-9218), analogous organic syntheses of small compound libraries (Chen et al., *J. Amer. Chem. Soc.* 116:2661 (1994)), oligocarbamates (Cho et al. (1993) *Science* 261:1303), and/or peptidyl phosphonates (Campbell et al. (1994) *J. Org. Chem.* 59:658), nucleic acid libraries (see Ausubel, Berger and Sambrook, all supra), peptide nucleic acid libraries (see, e.g., U.S. Pat. No. 5,539,083), antibody libraries (see, e.g., Vaughn et al. (1996) *Nature Biotechnology*, 14(3):309-314 and PCT Publication No. WO 1997/000271), carbohydrate libraries (see, e.g., Liang et al. (1996) *Science*, 274:1520-1522 and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment the invention, soluble assays using an astrovirus, or a cell or tissue expressing an astrovirus, either naturally occurring or recombinant are provided. In another embodiment, the invention provides solid phase based in vitro assays in a high throughput format, where the astrovirus is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for astrovirus in vitro, or for cell-based or membrane-based assays comprising an astrovirus. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book1* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-glycine sequences of between about 5 and 200 amino acids. Such flexible linkers are known to persons of skill in the art. For example, poly(ethelyne glycol) linkers are available from Shearwater Polymers, Inc. (Huntsville, Ala.). These linkers optionally have amide linkages, sulfhydryl linkages, or hetero functional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield (1963) *J. Am. Chem. Soc.* 85:2149-2154 (describing solid phase synthesis of, e.g., peptides); Geysen et al. (1987) *J. Immun. Meth.* 102:259-274 (describing synthesis of solid phase components on pins); Frank & Doring (1988) *Tetrahedron* 44:60316040 (describing synthesis of various peptide sequences on cellulose disks); Fodor et al. (1991) *Science,* 251:767-777; Sheldon et al. (1993) *Clinical Chemistry* 39(4):718-719; and Kozal et al. (1996) *Nature Medicine* 2(7):753759 (all describing arrays of biopolymers fixed to solid substrates). Non-chemical approaches for fixing tag binders to substrates include other common methods, such as heat, cross-linking by UV radiation, and the like.

Within certain aspects, astrovirus, proteins or peptides and immunogenic fragments thereof, and/or polynucleotides, as well as anti-astrovirus antibodies and/or T cells, may be incorporated into pharmaceutical compositions or immunogenic compositions (e.g., vaccines). Whole virus vaccine (live and attenuated, or replication incompetent, or killed) or subunit vaccines, such as structural or non-structural astrovirus proteins or immunogenic fragments thereof, of SEQ ID NO:2, SEQ ID NO:3, SEQ ID NO:4, SEQ ID NO:6, SEQ ID NO:7, SEQ ID NO:8, or conservatively modified variants thereof, can be used to treat or prevent astrovirus infections by eliciting an immune response in a subject. Alternatively, a pharmaceutical composition may comprise an antigen-presenting cell (e.g., a dendritic cell) transfected with an astrovirus polynucleotide such that the antigen-presenting cell expresses an astrovirus peptide.

Pharmaceutical compositions comprise one or more such vaccine compounds and a physiologically acceptable carrier. Vaccines may comprise, one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc;

an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Vaccine preparation is generally described in, for example, Powell and Newman, eds., *Vaccine Design* (the subunit and adjuvant approach), Plenum Press (NY, 1995). Vaccines may be designed to generate antibody immunity and/or cellular immunity such as that arising from CTL or CD4+ T cells.

Pharmaceutical compositions and vaccines within the scope of the present invention may also contain other compounds, which may be biologically active or inactive. For example, one or more immunogenic portions of other antigens may be present, either incorporated into a fusion polypeptide or as a separate compound, within the composition or vaccine. Polypeptides may, but need not, be conjugated to other macromolecules as described, for example, within U.S. Pat. Nos. 4,372,945 and 4,474,757. Pharmaceutical compositions and vaccines may generally be used for prophylactic and therapeutic purposes.

Nucleic acid vaccines encoding a genome, structural protein or non-structural protein or a fragment thereof of astrovirus can also be used to elicit an immune response to treat or prevent astrovirus infection. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA may be introduced using a viral expression system (e.g., vaccinia, pox virus, retrovirus, or adenovirus), which may involve the use of a non-pathogenic (defective), replication competent virus. Suitable systems are disclosed, for example, in Fisher-Hoch et al. (1989) *Proc. Natl. Acad. Sci. USA* 86:317-321; Flexner et al. (1989) *Ann. N.Y. Acad. Sci.* 569:86-103; Flexner et al. (1990) Vaccine 8:17-21; U.S. Pat. Nos. 4,603,112, 4,769,330, 4,777,127 and 5,017,487; WO 89/01973; GB 2,200,651; EP 0,345,242; WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; and Guzman et al. (1993) *Cir. Res.* 73:1202-1207. Techniques for incorporating. DNA into such expression systems are well known to those of ordinary skill in the art. The DNA may also be "naked," as described, for example, in Ulmer et al. (1993) *Science* 259:1745-1749 and reviewed by Cohen (1993) *Science* 259:1691-1692. The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the protein, the physician evaluates circulating plasma levels of the vector, vector toxicities, progression of the disease, and the production of anti-vector antibodies. In general, the dose equivalent of a naked nucleic acid from a vector is from about 1 μg to 100 μg for a typical 70 kilogram patient, and doses of vectors are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

All citations are herein incorporated by reference by their entireties.

EXAMPLE

Example 1

Genomic Acquisition of New Astrovirus Species

Samples and source: All stool samples are anonymized. Stool samples from South Asian are from children <15 years old who either have non-poliovirus acute flaccid paralysis (AFP) (n=57; mean age, 54.6 months) or are healthy household contacts of AFP patients (n=9; mean age, 27 months) or unrelated healthy children (n=41; mean age, 39.8 months) collected in Pakistan or Afghanistan. Stool samples from Nigeria are also from poliovirus negative children with AFP (n=96; mean age, 29.7 months).

Astrovirus group specific PCR. Stool samples are diluted 1:5 with Hank's Buffered Saline Solution (Gibco BRL), mixed with glass beads, vigorously vortexed and centrifuged twice at 5000 rpm for 10 minutes. Clarified supernatants (140 μl) are used for viral RNA extraction using RNAeasy mini kit (Qiagen). RNA is eluted in 50 μl of DEPC-treated water, immediately mixed with 40U of Ribolock RNase inhibitor and stored at −20° C. until reverse transcribed. Random octamer oligonucleotide (50 μmol; Europhin MWG Operon) is added to 10 μl of each extracted viral nucleic acid, the sample is denatured at 80° C. for 3 min, and then chilled on ice. A reaction mixture [9 μl containing 4 μl of 5× SuperScript buffer (Invitrogen), 1 μl of 100 mM dithiothreitol, 1.25 μl of 10 mM dNTP, and 200 U of SuperScript II reverse transcriptase (Invitrogen)] is added, and the reaction mixture is incubated at 25° C. for 10 min, 42° C. for 60 min, and 75° C. for 15 min and then chilled. PCR primers panAV-F11 (SEQ ID NO:9): 5'-GARTTYGATTGGRCKCGKTAYGA-3', panAV-F12 (SEQ ID NO:10): 5'-GARTTYGATTGGRCK-AGGTAYGA-3' and panAV-R1 (SEQ ID NO:11): 5'-GYTT-KACCCACATICCRAA-3' are used for the first round of hemi-nested PCR; while primer panAV-F21 (SEQ ID NO:12): 5'-CGKTAYGATGGKACKATICC-3', panAV-F22 (SEQ ID NO:13): 5'-AGGTAYGATGGKACKATICC-3' and panA-R1 are used for the second round of hemi-nested PCR. PCR primers used are similar to one described previously (Chu et al. (2008) *J. Virol.* 82:9107-14; Zhu et al. (2009) *J. Gen. Virol.* 90:883-87), with minor modifications. For the first round of nested PCR, 2 μl of each specimen cDNA is mixed with 5.2 μl of 10× TermoPol reaction buffer (New England Biolabs), 1.3 μl of 10 mM each dNTP, 50 μmol forward (both panAV-F11 and panAV-F12) and reverse primer, 1 μl of TaqDNA polymerase (New England Biolabs), and 31 μl of DEPC-treated water. The reaction is performed using initial denaturation at 95° C. for 3 min, followed by six cycles (95° C. for 40 sec, 50° C. for 1 min, and 68° C. for 1 min) and thirty-five cycles (95° C. for 30 sec, 52° C. for 30 sec, and 68° C. for 1 min), and final extension at 72° C. for 10 min. During first round of PCR, the first six cycles are done at low annealing temperature to facilitate primer hybridization by tolerating some nucleotide mismatches. For the second round of nested PCR, identical cycling conditions are used, with an annealing temperature of 55° C. for the first six cycles to increase specificity of primer hybridization and reduce background amplification. The reaction mixture for second round contained 0.5 μl of the PCR product from the first round mixed with 5.2 μl of 10× TermoPol reaction buffer (New England Biolabs), 1.25 μl of 10 mM each dNTP, 50 μmol of forward and reverse primer (both panAV-F21 and panAV-F22), 1 μl of TaqDNA polymerase (New England Biolabs), and 32.5 μl of DEPC-treated water. Products are visualized following electrophoresis on 1.5% agarose gel. PCR products showing positive bands of approximately 560 by corresponding to highly conserved RdRp gene are purified using a PCR purification kit (Qiagen) and directly sequenced from both direction.

Sequence independent viral nucleic acid amplification and 454 pyrosequencing. Stool sample supernatants are enriched for virus capsid protected nucleic acids followed by sequence independent amplification and 454 pyrosequencing as previously described (Kapoor et al. (2008) *PNAS* 105:20482-87 and Victoria et al. (2009) *J. Virol.* 83:4642-51). Sequence data is assembled using Sequencher 4.8 (genecode) and analyzed as described previously (Victoria et al. (2009) *J. Virol.* 83:4642-51).

Genome acquisition of HMOAstV and viral sequencing Pyrosequence derived sequence contigs showing significant tBLASTx hits to astroviruses (e-value of <0.001 in NCBI BlastX) are linked to the sequence of the RdRp gene obtained using pan-astrovirus PCR. To acquire the 3' end of viral genome, 10 μl of extracted RNA is mixed with 10 μmol of primer DT-01 (SEQ ID NO:14): 5'-ATTCTAGAGGCCGAG-GCGGCCGACAT-GTTTTTTTTTTTTTTTTTTTTTTTTTTTTTTVN-3' (Invitrogen), denatured at 75° C. for 5 min, and chilled on ice. Reaction mix [9 μl; containing 4 μl of 5× first-strand buffer (250 mM Tris/HCl, pH 8.3, 375 mM KCl, 15 mM MgCl$_2$; Invitrogen), 2 μl of 100 mM DTT, a 1 solution containing each dNTP at 10 mM, 8 units (0.2 μl) of recombinant RNase inhibitor (Promega), and 200 units of SuperScript III reverse transcriptase (Invitrogen)] is then added and incubated at 52° C. for 30 min, followed by 75° C. for 10 min. Two units of RNase H (New England Biolabs) is added, and the reaction mixture is further incubated for 10 min at 37° C. PCR is performed using a virus-specific primer, 295-3end-F1 (SEQ ID NO:15): 5'-GTCAATACCATCTACTGGGCA-3', and DT-02 (SEQ ID NO:16): 5'-ATTCTAGAGGCCGAGGCG-GCC-3'. The PCR consists of an activation step of 5 mM at 95° C. followed by thrity-five cycles of amplification at 95° C. for 1 min, 60° C. for 30 sec, and 72° C. for 2 min.

To acquire the 5' end of the HMOAstV-A-NI-295 genome, 10 µl of extracted RNA is mixed with 10 µmol of virus specific-primer 295-Send-R-1 (SEQ ID NO:17): 5'-GGTTTTTACTGGTGTAGTTACTGG-3', denatured at 75° C. for 5 min, and chilled on ice. A reverse transcription reaction mix similar to that used for 3' RACE is added, and the reaction mixture is incubated at 52° C. for 30 min, followed by 75° C. for 10 min. Two units of RNase H is then added, and the reaction mixture is further incubated for 10 min at 37° C. cDNA is purified using a Qiagen PCR purification kit, and a poly(C) tail is added using terminal deoxynucleotide transferase (New England Biolabs) and dCTP. PCR is performed using the HMOAstV-A-NI-295 specific primers 295-Send-R-2 (SEQ ID NO:18): 5'-ACTGGTGTAGTTACTGGCTG-CAC-3' and PPC01 (SEQ ID NO:19): 5'-GGCCACGCGTC-GACTAGTACGGGIIGGGIGGGGIGG-3', where I is deoxyinosine. PCR cycles consists of 5 min at 95° C. followed by thirty-five cycles of amplification 95° C. for 1 min, 60° C. for 30 sec, and 72° C. for 1 min. PCR products are then directly sequenced or cloned using pGEM-T ease vector (Promega) and then sequenced.

Example 2

Classification of Astroviruses Circulating in Humans

An RT-PCR assay using primers that targets conserved motifs in the RdRp gene of diverse astroviruses (Zhu et al. (2009) *J. Gen. Viral.* 90:883-87) is used to screen human stool supernatants. Stools from cases of non-poliovirus AFP from Nigeria and Pakistan are initially screened. All positive pan-astrovirus PCR amplicons are then directly sequenced. Of 39 astrovirus positive samples, 27 are found to be closely related to human astrovirus (HAstV) (FIG. 1). Astrovirus MLB (AstV-MLB) is the second reported species of human astrovirus; it was described in 2008 as isolated from a stool sample of an American child with acute gastroenteritis (Finkbeiner et al. (2008) *Viral. J.* 5:117). Astrovirus sequences from four Nigerian children suffering from non-polio AFP are closely related to AstV-MLB (>95% nucleotide identity) and hence represents cases of AstV-MLB infection in Nigeria (FIG. 1). It is not known whether these paralyzed children has diarrhea at time of collection.

TABLE 1a

Pairwise amino acid sequence identity between astrovirus species. ORF1b (RdRp) identities are in bold fonts and ORF2 (complete capsid) identities are in regular fonts.

|  | HAstV-1 | HAstV-2 | HAstV-3 | HAstV-4 | HAstV-5 | HAstV-6 | HAstV-7 | HAstV-8 |
|---|---|---|---|---|---|---|---|---|
| HAstV-1 |  | 70.7 | 98.0 | 64.3 | 70.5 | 70.9 | 83.3 | 71.8 |
| HAstV-2 | 96.5 |  | 71.4 | 65.7 | 66.1 | 67.2 | 70.1 | 70.7 |
| HAstV-3 | 93.8 | 93.0 |  | 65.2 | 71.4 | 71.9 | 84.7 | 72.7 |
| HAstV-4 | 97.9 | 95.9 | 94.3 |  | 64.8 | 66.4 | 63.7 | 72.1 |
| HAstV-5 | 95.0 | 92.4 | 95.7 | 95.0 |  | 74.7 | 72.1 | 74.9 |
| HAstV-6 | 95.7 | 93.7 | 96.2 | 96.7 | 98.1 |  | 71.8 | 73.6 |
| HAstV-7 | 95.3 | 93.0 | 96.7 | 96.2 | 97.6 | 98.6 |  | 70.9 |
| HAstV-8 | 98.3 | 96.5 | 94.8 | 97.9 | 95.9 | 96.7 | 96.2 |  |
| AstV-MLB1 | 56.1 | 56.2 | 59.1 | 55.7 | 57.4 | 59.1 | 59.1 | 55.7 |
| BAstV-1 | 46.8 | 52.9 | 51.2 | 46.8 | 46.8 | 50.2 | 49.8 | 46.4 |
| MAstV | 50.4 | 53.2 | 53.9 | 50.4 | 49.6 | 53.9 | 53.9 | 49.6 |
| OAstV | 50.2 | 54.7 | 52.6 | 49.8 | 49.0 | 52.6 | 52.6 | 49.4 |
| HMOAstV-A | 51.0 | 52.3 | 55.0 | 51.0 | 51.0 | 55.0 | 54.5 | 50.2 |
| HMOAstV-B | 51.5 | 51.7 | 55.5 | 51.0 | 51.5 | 54.5 | 54.0 | 51.0 |
| TAstV-1 | 36.8 | 40.9 | 39.8 | 36.4 | 36.8 | 38.3 | 38.3 | 36.4 |

Eight of the 39 pan-astrovirus PCR positive amplicons show significant clustering with Mink and Ovine astrovirus species (MAstV and OAstV; FIG. 1). These putative novel astroviruses are therefore called human mink and ovine-like astroviruses (HMOAstV). Alignments of the partial RdRp protein sequences of HMOAstV, MAstV, OAstV, BAstV (Bat), MLB and HAstV species are used to calculate genetic distances between different astrovirus species and between the eight known serotypes of HAstV (Table 1a and 1b).

TABLE 1b

Pairwise amino acid sequence identity between astrovirus species. ORF1b (RdRp) identities are in bold fonts and ORF2 (complete capsid) identities are in regular fonts.

|  | AstV-MLB1 | BAstV-1 | MAstV | OAstV | HMOAstV-A | HMOAstV-B | TAstV-1 |
|---|---|---|---|---|---|---|---|
| HAstV-1 | 26.1 | 24.8 | 21.7 | 23.3 | 23.5 | 23.3 | 18.3 |
| HAstV-2 | 25.0 | 24.9 | 22.3 | 22.0 | 23.9 | 23.2 | 18.1 |
| HAstV-3 | 26.4 | 25.0 | 21.8 | 23.5 | 23.5 | 23.2 | 18.4 |
| HAstV-4 | 23.9 | 25.0 | 22.5 | 23.6 | 23.0 | 23.9 | 18.1 |
| HAstV-5 | 26.7 | 25.4 | 22.7 | 22.5 | 23.1 | 23.6 | 17.5 |
| HAstV-6 | 25.8 | 25.6 | 24.0 | 21.8 | 23.9 | 23.5 | 18.6 |
| HAstV-7 | 25.6 | 25.0 | 22.1 | 22.8 | 23.3 | 23.0 | 19.1 |
| HAstV-8 | 26.7 | 25.0 | 22.3 | 22.8 | 23.0 | 23.3 | 18.4 |
| AstV-MLB1 |  | 22.7 | 21.4 | 21.8 | 21.6 | 20.8 | 18.6 |
| BAstV-1 | 43.2 |  | 28.3 | 28.2 | 29.1 | 27.0 | 18.8 |
| MAstV | 47.2 | 56.8 |  | 40.2 | 46.4 | 42.2 | 21.2 |

TABLE 1b-continued

Pairwise amino acid sequence identity between astrovirus species. ORF1b (RdRp) identities are in bold fonts and ORF2 (complete capsid) identities are in regular fonts.

| | AstV-MLB1 | BAstV-1 | MAstV | OAstV | HMOAstV-A | HMOAstV-B | TAstV-1 |
|---|---|---|---|---|---|---|---|
| OAstV | 50.2 | 55.3 | 66.1 | | 39.9 | 40.7 | 20.8 |
| HMOAstV-A | 48.9 | 56.1 | 66.5 | 63.5 | | 51.9 | 20.5 |
| HMOAstV-B | 48.5 | 55.7 | 65.7 | 61.9 | 75.1 | | 19.8 |
| TAstV-1 | 38.6 | 38.7 | 37.0 | 39.0 | 39.0 | 39.0 | |

Based on the genetic distances between established human and animal astrovirus species, we conclude that two new species of genus *Mastrovirus* are identified, since the genetic distances between them is greater than that seen amongst the eight serotypes of HAstV strains in the RdRp region. HMOAstV species A is found in two Nigerian (NI-281 and NI-295) and one Pakistani child (PK-6187). HMOAstV species B is found in one child from Nigeria and Pakistan (Table 2).

TABLE 2

Astrovirus detected in different human stool groups

| | Total | HAstV | AstV-MLB | HMOAstV-A/B |
|---|---|---|---|---|
| Nigeria-AFP | 95 | 14 | 4 | 3 |
| Pakistan-AFP | 43 | 1 | 0 | 2 |

Example 3

Acquisition of a Full HMOAstV Genome

To acquire the complete genome of an HMOAstV species, the stool samples of Nigerian patients NI-295 are subjected to highly parallel pyrosequencing. 4093 individual reads are assembled into longer sequence contigs (Victoria et al. (2009) *J. Virol.* 83:4642-51). Assembled contigs and singlets are then analyzed using BLASTx. In sample NI-295, three sequences, two derived from contigs and one singlet, show significant (E-score <0.001) similarity to ORF1ab and at the 5' end of ORF2 in MAstV. One of the three sequences overlapped with sequence obtained by pan-PCR. The remaining genomic sequence of HMOAstV-A-NI-295 is acquired using PCR to link the available fragments and 5' and 3' RACE to acquire the viral RNA extremities. Additional genomic sequences of HMOAstV-B-NI-196 are acquired using degenerate primers targeting conserved motifs in ORF2 of astroviruses and 3' RACE.

Genomic features of an HMOAstV. HMOAstV-A-NI295 prototype is 6534 nt long, excluding its 3' poly A tail. HMOAstV-A-N1295 has untranslated regions (UTRs) of 42 nucleotides at the 5' (with a 16 nucleotide stem loop from position 14 to 29) and of 117 nucleotides at the 3' ends of the genome. The 3 UTR is of variable length for HMOAstV species A and B being 117 and 106 nucleotide long respectively, excluding the polyA tail. As found in other astroviruses the 3'UTR also contains a highly conserved stem-loop II-like motif. This motif is also reported to be present in several coronavirus and picornavirus (Jonassen et al. (2001) *J. Gen. Virol.* 82:1061-67). An expected retrovirus-like ribosomal frameshift signal (Marczinke et al. (1994) *J. Virol.* 68:5588-95) is found in the 23 nucleotide overlap region between ORF1a and ORF1b of HMOAstV-A-NI295, consisting of the heptameric AAAAAAC sequence from nt 2657 to 2663, followed by a potential 20 nt long pseudo knot sequence from nt 2672 to 2692 (predicted using mFold RNA fold server at mfold.bioinfospi.edu/cgi-bin/rna-form1.cgi). The predicted size of ORF1a, ORF 1 ab and ORF2 are 874, 1395, and 731 amino acids, respectively. The consensus promoter sequence initiating ORF2 subgenomic RNA synthesis in other astroviruses (Jonassen et al. (2001) J. Gen. Virol. 82:1061-67), differed by 6 to 8 nucleotides from those of the three HMOAstV species (consensus CUUUGGAGGGGMGGWCCAAAGY-DWRGWB AUGGC; SEQ ID NO:20) with the methionine codon in optimal Kozak's context (RNNAUGG, where R=A/G). Analysis of ORF1a suggests the presence of five transmembrane helices (TMH) located between amino acid positions 167-186, 251-273, 280-302, 317-336 and 357-379 (www.cbs.dtu.dk/services/TMHMM/). A trypsine like serine protease domain is found between amino acid positions 431-618, and similar to other astroviruses contained a histidine (amino acid position 476), aspartate (amino acid position 505) and serine (amino acid position 568) residues. A potential conserved proteolytic cleavage site, which is conserved among ovine, mink, MLB and HAstV astroviruses, is found at end of protease (VHQ/TNT). Astroviruses, unlike other RNA viruses, lack highly conserved domains for helicase and viral genome linked protein (VPg) (Al-Mutairy et al. (2005) Virus genes 31: 21-30).

The characteristic YGDD (SEQ ID NO:21) RdRp motif is encoded by the ORF1b. Complete ORF2 of HMOAstV-A-NI-295 is predicted to code for a 731 amino acid long protein of 80 kda while the ORF2 of HMOAstV-B-NI196 encodes a 755 amino acid long protein. The conserved N-terminal half of the capsid precursor has been proposed as the core assembly domain of the viral capsid (Jonassen et al. (2001) *J. Gen. Virol.* 82:1061-67; Krishna (2005) *Viral Immunol.* 18:17-26). A highly conserved basic stretch in the N-terminal part of the capsid precursor of HAstV, FAstV (feline), PAstV (porcine), and TAstV-2 (turkey) is also present in the corresponding region of HMOAstV species. However, in contrast to other HAstV and like mink and ovine astroviruses, neither HMOAstV species show the presence of the SR dipeptide (Jonassen et al. (2001) *J. Gen. Virol.* 82:1061-67).

Example 4

Phylogenetic Analysis

To determine the sequence divergences between HMOAstV species and those of other astroviruses, at least one representative virus member from each species of the two currently classified genera of family Astroviridae are aligned. Sequences used for the comparison comprised the following: for the genus *Mamstrovirus*, HAstV isolate V1182 (GenBank accession number AB325804); HAstV1 (NC_001943); HAstV2 (L13745); HAstV3 (EMBL accession no. AAD17224); HAstV4 (GenBank DQ070852); HAstV5 (DQ028633); HAstV6 (EMBL: CAA86616); HAstV7

(AAK31913); HAstV8 (GenBank AF260508); HAstV-MLB1 (NC_011400); OAstV (NC_002469); MAstV (NC_004579); and BAstV (bat; EU847155); and for the genus *Avastrovirus*, duck astrovirus C-NGB (Genbank accession no. NC_012437), TAstV-1 (turkey; Y15936); TAstV-2 (turkey; NC_005790); TAstV-3 (turkey; AY769616) and Chicken Astrovirus (NC_003790). Phylogenetic analyses of ClustalW aligned regions are carried out by neighbor joining of nucleotide or amino acid p-distances implemented in the program MEGA4. Bootstrap resampling is carried out to demonstrate robustness of groupings.

Figure 2A:
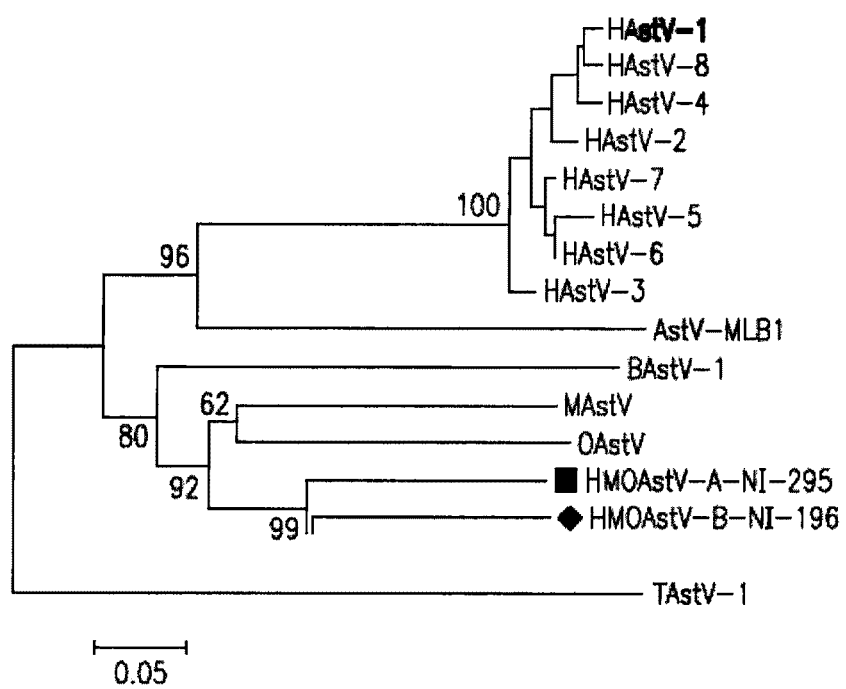
FIG. 2A shows the tree based on ORF1b region (corresponding to amino acid position 1192 to 1431 of ORF1b of the reference HAstV-1 genome NC_001943, protein ID NP_059443).
Figure 2B:
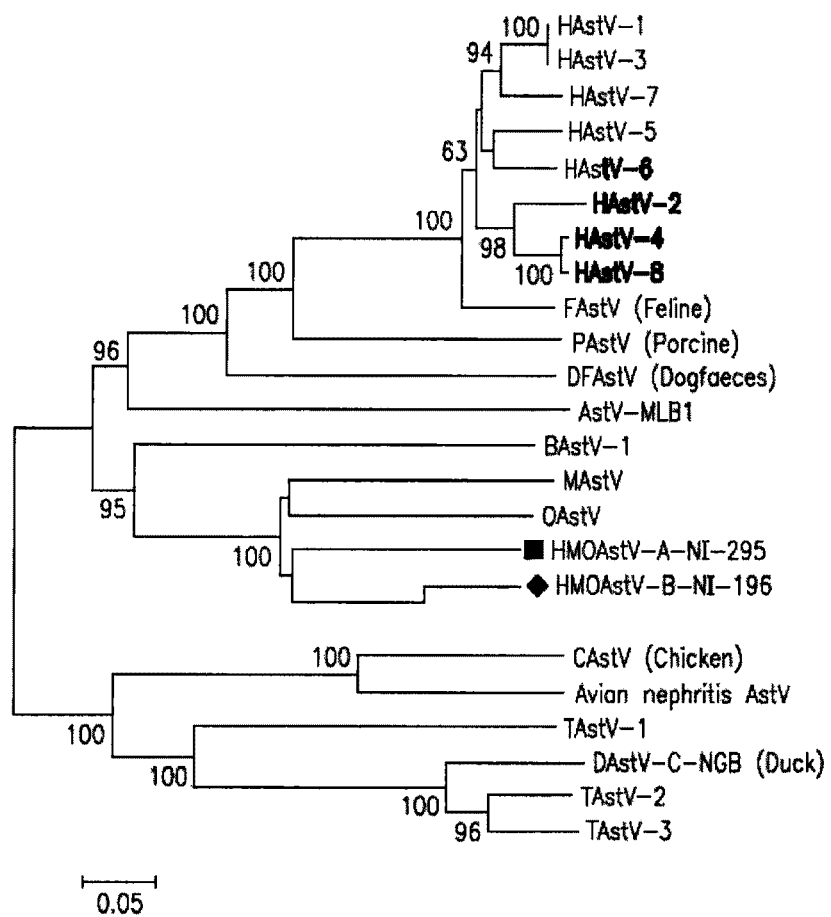
FIG. 2B shows the tree based on the N-terminus of ORF2 (corresponding to amino acid position 1 to 381 of ORF2-capsid of the reference HAstV-1 protein NP_05944). Phylogenetic trees are produced using the neighbour-joining method implemented in the program MEGA4. Numbers at nodes indicate bootstrap percentages obtained using 1000 replicates.
Figure 3:
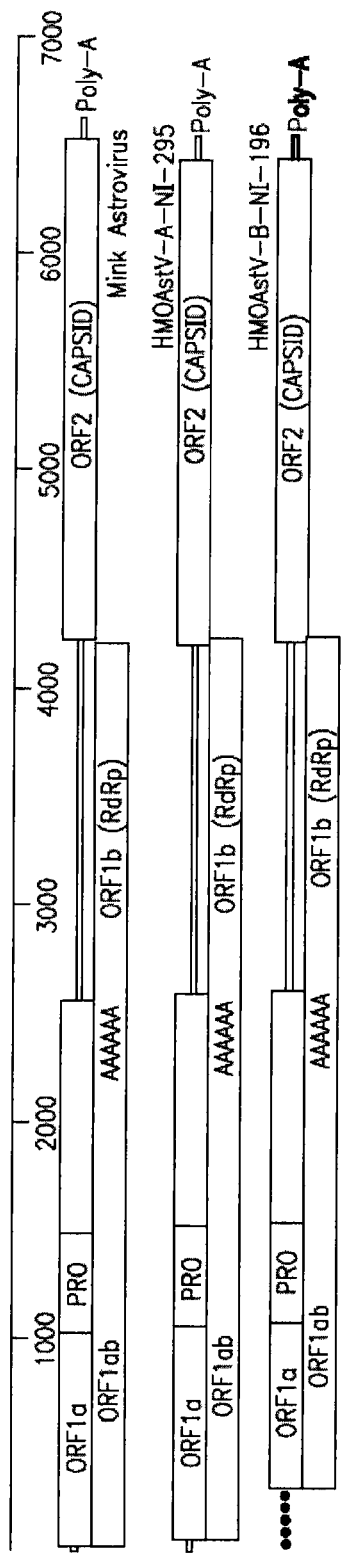
FIG. 3 shows schematic diagrams of the mink astrovirus (MAstV) genome and novel human astrovirus (HMOAstV) species A (complete genome), and species B (partial genomes). The 5' and 3' untranslated regions (UTRs), ORFs, protease motif (PRO), RdRp motif, ribosomal slippage site (AAAAAA) and polyA tail at 3' end are shown. The dotted box shows partial RdRp region amplified by pan-astrovirus PCR that was used for the phylogenetic analysis shown in FIG. 1.

Phylogenetic analysis of the new astrovirus species. The complete genome HMOAstV-A-NI295, and partial genomes of HMOAstV-B-NI196 are acquired and used for viral protein alignments. Regions of amino acid sequence similarities are readily apparent in the ORF1b region of the genomes, including highly conserved amino acid motifs in the active site of the RdRp gene. Phylogenetic of the longer RdRp sequence showed both species to be equidistant (FIG. 2A). The amino-termini region of the capsid protein coded by ORF2 is also conserved among astroviruses while the carboxyl-terminal region alignment is highly problematic (Jonassen et al. (2001) *J. Gen. Virol.* 82:1061-67). Therefore, only the region of the capsid genes that can be readily aligned is used for phylogenetic analysis. The HMOAstV species A and B appear equidistant in genetic distance in the RdRp region (Table 1a, Table 1b, and FIG. 2A). The extended phylogenetic analyses therefore confirms the relationship of the new novel human astroviruses with mink and ovine astroviruses and that both HMOAstV species appear to be derived from a common ancestor.

Here human stools samples are collected from different continents for the presence of known and new astroviruses. Two new human astroviruses species in the genus *Mamastrovirus* are identified and appear phylogentically related to each other and closest to the Mink and Ovine astroviruses and hence provisionally named human mink and ovine-like astro virus species A and B (HMOAstV-A and HMOAstV-B).

Different species of the Astroviridae family of small RNA viruses are known to cause diarrhea in mammalian and avian hosts (Mendez & Arias (2007) Astroviridae. In *Fields Virology*, pp. 981-1000. Edited by D. M. Knipe and P. M. Howley. Philadelphia: Lippincott Williams & Wilkins; Monroe et al. (2005) Astroviridae. In *Virus Taxonomy. Eighth Report of the International Committee on Taxonomy of Viruses*, pp. 859-64. Edited by C. M. Fauquet, M. A. Mayo, J. Maniloff, U. Desselberger and L. A. Ball. Amsterdam Elsevier Academic Press). The present invention provides new related species in human stools from two continents. Understanding the genetic diversity within viral families infecting humans can enable the design of specific diagnostic assays (Gutierrez-Aguirre et al. (2008) *J. Clin. Mivrobiol.* 46:2547-54; Kapoor et al. (2009) *J. Infect. Dis.* 199:196-200; Liu et al. (2008) *Virology* 375:301-06; Patel et al. (2004) *J. Virol. Methods* 120:167-72). The most common astrovirus detected by this pan-astrovirus PCR approach is HAstV (n=27) indicating that it is likely the dominant human astrovirus species. HAstV is also detected in 12/95 diarrhea cases and none of the matched controls confirming its known role in gastroenteritis. Four variants of the second reported human astrovirus species (AstV-MLB) are detected in Nigeria, while HMOAstV-A and HMOAstV-B are detected reflecting an approximately 3 fold lower prevalence of HMOAstV relative to HAstV (Table 2).

Accordingly to ICTV guideline Astrovirus species are currently "defined on the basis of host of origin" (www.ncbi.nlm.nih.gov/ICTVdb/Ictv/fs_astro.htm#Genus1). Therefore based on current ICTV guideline all HAstV serotypes, AstV-MLB, HMOAstV-A and HMOAstV-B can be classified as the same group of viral species. The identification of multiple lineages of human astrovirus (HAstV, AstV-MLB, and HMOAstV disclosed here) phylogenetically separated by different lineages of animal astroviruses likely represents independent origins for each of these lineages (Finkbeiber et al. (2008) Virol. J. 5:117). Based on currently available sequence data possible sources of the human astrovirus lineage are the animal species hosting the most closely related viral species namely felines for HAstV and mink or sheep for HMOAstV. The identification of highly divergent turkey astrovirus (TAstV) with duck astrovirus being more closely related to TAstV2/3 than to TAstV 1 may similarly be interpreted as past transmission of astroviruses from turkeys to ducks (Fu et al. (2009) J. Gen. Virol. 90:1104-08; Todd et al. (2009) Avian Pathol. 38:21-30). A recent phylogenetic analysis of bat astroviruses RdRp sequences also showed a surprisingly high level of genetic diversity with different bad species and even different bat genus and families infected with closely related astroviruses as well as highly divergent astrovirus lineages infecting the same bat species (Chu et al. (2008) J. Virol. 82:9107-14; Zhu et al. (2009) J. Gen. Virol. 90:883-87). Since highly divergent astrovirus lineages can infect the same animal species and the possibility of cross-species transmissions, we suggest that astroviruses be grouped and named based on both host species and a genetic distance criteria using either the capsid or RdRp loci. Serotypes may be designed by a future letter (e.g., HAstV1a to HAstV1h for the right serotypes of HAstV, HAstV2 for AstV-MLB, HAstV3 for HMOAstV-A, and HAstV4 for HMOAstV-B). A group of astroviruses with closely related capsid sequences infecting multiple animal species may be named after the earliest reported host species. Alternatively, the host species name may be avoided altogether and simple numerical labeling used for astrovirus phylogenetic clusters (e.g., AstV1, AstV2, etc).

What is claimed is:

1. A recombinant vector comprising an operative promoter and a heterologous nucleic acid molecule comprising:
   a) A sequence selected from the group consisting of SEQ ID NO:1, SEQ ID NO:5, or the full-length complement thereof,
   b) A sequence comprising at least 50, 100, 150 contiguous nucleotides of SEQ ID NO:1, SEQ ID NO:5, or the full-length complement thereof, or
   c) A sequence having at least 75% identity to SEQ ID NO:1, SEQ ID NO:5, or a full-length complement thereof.

2. The recombinant vector of claim 1, wherein the nucleic acid molecule comprises at least 50, 100 or 150 contiguous nucleotides of SEQ ID NO:1, SEQ ID NO:5, or the full-length complement thereof.

3. The recombinant vector of claim 1, wherein the sequence is at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:1, SEQ ID NO:5, or the full-length complement thereof.

4. An isolated host cell comprising the recombinant vector of claim 1.

5. A method of detecting an astrovirus nucleic acid comprising:
   (a) contacting a sample suspected of containing an astrovirus nucleic acid with a nucleic acid molecule comprising at least 50, 100 or 150 contiguous nucleotides of SEQ ID NO:1, SEQ ID NO:5, or the full-length complement thereof; and (b) detecting the presence or absence of hybridization.

6. A method of detecting an astrovirus nucleic acid comprising:
   (a) amplifying the nucleic acid of a sample suspected of containing an astrovirus nucleic acid with at least one nucleic acid molecule comprising at least 50, 100 or 150 contiguous nucleotides of SEQ ID NO:1, SEQ ID NO:5, or the full-length complement thereof, to produce an amplification product; and
   (b) detecting the presence of an amplification product, thereby detecting the presence of the astrovirus nucleic acid.

7. A kit for detecting an astrovirus nucleic acid comprising a detectable label attached to an isolated nucleic acid molecule comprising at least 50, 100 or 150 contiguous nucleotides of SEQ ID NO:1, SEQ ID NO:5, or the full-length complement thereof.

8. A method of assaying for an anti-astrovirus compound comprising:
   (a) contacting a sample containing an astrovirus comprising a nucleotide sequence having at least 75% identity to SEQ ID NO:1, SEQ ID NO:5, or a full-length complement thereof, with a test compound; and
   (b) determining whether the test compound inhibits astrovirus replication, wherein inhibition of astrovirus replication indicates that the test compound is an anti-astrovirus compound.

* * * * *